(12) United States Patent
Loh et al.

(10) Patent No.: US 12,151,094 B2
(45) Date of Patent: Nov. 26, 2024

(54) NON-INVASIVE NERVE STIMULATOR WITH BATTERY MANAGEMENT

(71) Applicant: Neurostim Technologies LLC, Waltham, MA (US)

(72) Inventors: Alan E. Loh, Los Altos, CA (US); Michael Bernard Druke, Half Moon Bay, CA (US); Brian Gagne, Williston, VT (US); William Conrad Altmann, Austin, TX (US)

(73) Assignee: Neurostim Technologies LLC, Waltham, MA (US)

( * ) Notice: Subject to any disclaimer, the term of this patent is extended or adjusted under 35 U.S.C. 154(b) by 206 days.

(21) Appl. No.: 17/585,921

(22) Filed: Jan. 27, 2022

(65) Prior Publication Data

US 2022/0233844 A1 Jul. 28, 2022

Related U.S. Application Data

(60) Provisional application No. 63/142,362, filed on Jan. 27, 2021.

(51) Int. Cl.
*A61N 1/04* (2006.01)
*A61N 1/36* (2006.01)

(52) U.S. Cl.
CPC ......... *A61N 1/0456* (2013.01); *A61N 1/0492* (2013.01); *A61N 1/36007* (2013.01); *A61N 1/36034* (2017.08)

(58) Field of Classification Search
CPC .......................... A61N 1/0456; A61N 1/36034
(Continued)

(56) References Cited

U.S. PATENT DOCUMENTS

| 5,914,585 A | 6/1999 | Grabon |
| 6,184,654 B1 | 2/2001 | Bachner, III et al. |

(Continued)

FOREIGN PATENT DOCUMENTS

| JP | 2017526496 A | 9/2017 |
| KR | 100397119 B1 | 9/2003 |

(Continued)

OTHER PUBLICATIONS

Furset, K, et al.; High Pulse Drain Impact on CR2032 Coin Cell Battery Capacity; 2011.
(Continued)

*Primary Examiner* — Nadia A Mahmood
(74) *Attorney, Agent, or Firm* — Potomac Law Group, PLLC

(57) ABSTRACT

A topical nerve stimulation patch includes a substrate, a dermis conforming bottom surface of the substrate, a top outer surface of the substrate, a plurality of electrodes positioned on the patch proximal to the bottom surface and located beneath the top outer surface and coupled to the substrate, a power source and electronic circuitry embedded in the patch and located beneath the top outer surface and coupled to the substrate. The electronic circuitry is configured to generate an electrical stimuli via the electrodes that comprise a plurality of pulses of a target output voltage, and includes a controller configured to generate a first pulse at a first output voltage that is less than the target output voltage and generate a second pulse at a second output voltage that is less than the target output voltage and greater than the first output voltage.

20 Claims, 15 Drawing Sheets

(58) Field of Classification Search
USPC .......................................................... 607/41
See application file for complete search history.

(56) References Cited

U.S. PATENT DOCUMENTS

| | | |
|---|---|---|
| 7,034,677 B2 | 4/2006 | Steinthal et al. |
| 7,504,948 B2 | 3/2009 | Wulff et al. |
| 7,618,260 B2 | 11/2009 | Daniel et al. |
| 7,663,490 B2 | 2/2010 | Dishongh |
| 8,001,400 B2 | 8/2011 | Fadell |
| 8,212,650 B2 | 7/2012 | Tsern et al. |
| 8,308,665 B2 | 11/2012 | Harry et al. |
| 8,394,009 B2 | 3/2013 | Bolyard et al. |
| 8,498,428 B2 | 7/2013 | Schreuder et al. |
| 8,612,002 B2 | 12/2013 | Faltys et al. |
| 8,639,319 B2 | 1/2014 | Hugh et al. |
| 8,793,522 B2 | 7/2014 | Rahman et al. |
| 8,855,767 B2 | 10/2014 | Faltys et al. |
| 8,898,496 B1 | 11/2014 | Chi |
| 8,902,315 B2 | 12/2014 | Fisher et al. |
| 8,926,509 B2 | 1/2015 | Magar et al. |
| 9,130,651 B2 | 9/2015 | Tabe |
| 9,162,064 B2 | 10/2015 | Faltys et al. |
| 9,241,669 B2 | 1/2016 | Pugh et al. |
| 9,407,755 B1 | 8/2016 | Koller et al. |
| 9,415,158 B2 | 8/2016 | Miller et al. |
| 9,418,551 B2 | 8/2016 | Kavaler et al. |
| 9,564,761 B2 | 2/2017 | Hopfer, III et al. |
| 9,736,779 B2 | 8/2017 | Min et al. |
| 9,749,955 B2 | 8/2017 | Min et al. |
| 9,750,455 B2 | 9/2017 | Bolognia |
| 9,779,555 B2 | 10/2017 | Chang et al. |
| 9,826,482 B2 | 11/2017 | Park et al. |
| 9,860,352 B2 | 1/2018 | Fisher et al. |
| 9,871,004 B2 | 1/2018 | Zhai |
| 9,882,413 B2 | 1/2018 | Jeong |
| 9,897,661 B2 | 2/2018 | Nelson et al. |
| 9,974,461 B2 | 5/2018 | Shin et al. |
| 9,979,225 B2 | 5/2018 | Bernhard |
| 10,009,852 B2 | 6/2018 | Law et al. |
| 10,021,239 B2 | 7/2018 | Ledingham et al. |
| 10,110,046 B1 | 10/2018 | Esquibel et al. |
| 10,226,575 B2 | 3/2019 | Miller et al. |
| 10,243,412 B1 | 3/2019 | Fink et al. |
| 10,257,885 B2 | 4/2019 | Chung |
| 10,261,568 B2 | 4/2019 | Jensen et al. |
| 10,303,122 B2 | 5/2019 | Choi et al. |
| 10,326,295 B2 | 6/2019 | Zuerner |
| 10,344,924 B1 | 7/2019 | Ganahl |
| 10,416,241 B2 | 9/2019 | Matsumura et al. |
| 10,447,178 B1 | 10/2019 | Hays et al. |
| 10,455,639 B2 | 10/2019 | Holmes et al. |
| 10,468,906 B2 | 11/2019 | Yang et al. |
| 10,511,180 B2 | 12/2019 | Oikarinen et al. |
| 10,518,792 B2 | 12/2019 | Denny et al. |
| 10,520,448 B2 | 12/2019 | Ziltz et al. |
| 10,670,202 B2 | 6/2020 | Ganahl |
| 10,779,092 B2 | 9/2020 | Jürg et al. |
| 10,863,060 B2 | 12/2020 | Kokonaski et al. |
| 10,893,576 B2 | 1/2021 | Strecker |
| 10,915,722 B2 | 2/2021 | Codato et al. |
| 10,973,452 B2 | 4/2021 | Fecteau et al. |
| 11,031,822 B2 | 6/2021 | Zeine et al. |
| 11,051,095 B2 | 6/2021 | Cramer et al. |
| 11,071,456 B2 | 7/2021 | Hunter et al. |
| 11,101,634 B2 | 8/2021 | Gupta et al. |
| 2009/0076343 A1 | 3/2009 | James et al. |
| 2009/0132018 A1 | 5/2009 | DiUbaldi et al. |
| 2010/0049006 A1 | 2/2010 | Magar et al. |
| 2011/0190849 A1 | 8/2011 | Faltys et al. |
| 2012/0176237 A1 | 7/2012 | Tabe |
| 2012/0316471 A1 | 12/2012 | Rahman et al. |
| 2013/0013022 A1 | 1/2013 | Júnior |
| 2013/0135097 A1 | 5/2013 | Doezema |
| 2013/0331910 A1 | 12/2013 | Amont et al. |
| 2014/0074186 A1 | 3/2014 | Faltys et al. |
| 2014/0194782 A1 | 7/2014 | Rahman et al. |
| 2014/0299169 A1 | 10/2014 | Schneider et al. |
| 2015/0188389 A1 | 7/2015 | Wan et al. |
| 2015/0289814 A1 | 10/2015 | Magar et al. |
| 2016/0000300 A1 | 1/2016 | Williams |
| 2016/0059108 A1 | 3/2016 | Demolder |
| 2016/0105162 A1 | 4/2016 | Zangi et al. |
| 2016/0239710 A1 | 8/2016 | Chen |
| 2016/0344441 A1 | 11/2016 | Shah et al. |
| 2016/0353386 A1 | 12/2016 | Sasidharan et al. |
| 2017/0025991 A1 | 1/2017 | Chou et al. |
| 2017/0026908 A1 | 1/2017 | Shi et al. |
| 2017/0054900 A1 | 2/2017 | Chien et al. |
| 2017/0100046 A1 | 4/2017 | Roh et al. |
| 2017/0259072 A1 | 9/2017 | Newham et al. |
| 2017/0280498 A1 | 9/2017 | Min et al. |
| 2017/0312512 A1 | 11/2017 | Creasey et al. |
| 2017/0312576 A1 | 11/2017 | Natarajan et al. |
| 2018/0115171 A1 | 4/2018 | Boesen |
| 2018/0161587 A1* | 6/2018 | Beyer ..................... A61N 1/18 |
| 2018/0280708 A1 | 10/2018 | Escalona et al. |
| 2018/0330386 A1 | 11/2018 | Kim |
| 2019/0104992 A1 | 4/2019 | Magar et al. |
| 2019/0125266 A1 | 5/2019 | Magar et al. |
| 2019/0151539 A1 | 5/2019 | Miller et al. |
| 2019/0172571 A1 | 6/2019 | Ramaci |
| 2019/0303945 A1 | 10/2019 | Mitra et al. |
| 2019/0321636 A1 | 10/2019 | Law et al. |
| 2019/0343461 A1 | 11/2019 | Magar et al. |
| 2019/0357794 A1 | 11/2019 | Bardy et al. |
| 2019/0359351 A1 | 11/2019 | Fisher et al. |
| 2019/0360940 A1 | 11/2019 | Ziltz et al. |
| 2020/0007053 A1 | 1/2020 | Hays et al. |
| 2020/0054889 A1 | 2/2020 | Makansi |
| 2020/0067327 A1 | 2/2020 | Oikarinen et al. |
| 2020/0076420 A1 | 3/2020 | Ding et al. |
| 2020/0106257 A1 | 4/2020 | Gupta et al. |
| 2020/0187752 A1 | 6/2020 | Williams |
| 2020/0228166 A1 | 7/2020 | Scherer et al. |
| 2020/0297269 A1 | 9/2020 | Vieri |
| 2020/0334972 A1 | 10/2020 | Gopalakrishnan |
| 2020/0335211 A1 | 10/2020 | Gopalakrishnan |
| 2020/0338358 A1 | 10/2020 | Makansi |
| 2020/0406033 A1* | 12/2020 | Loh ..................... A61N 1/36007 |
| 2021/0052026 A1 | 2/2021 | Albaugh et al. |
| 2021/0059542 A1 | 3/2021 | Gopalakrishnan |
| 2021/0074421 A1 | 3/2021 | Gopalakrishnan |
| 2021/0093876 A1 | 4/2021 | Montague et al. |
| 2021/0173093 A1 | 6/2021 | Redler et al. |
| 2021/0176557 A1 | 6/2021 | Schreuder |
| 2021/0185837 A1 | 6/2021 | Martin et al. |
| 2021/0218438 A9 | 7/2021 | Scherer et al. |
| 2021/0265054 A1 | 8/2021 | Kosman et al. |

FOREIGN PATENT DOCUMENTS

| | | |
|---|---|---|
| KR | 1020140098782 A | 8/2014 |
| WO | 2006116718 A2 | 11/2006 |
| WO | 2009064641 A1 | 5/2009 |
| WO | 2010075115 A2 | 7/2010 |
| WO | 2015183620 A2 | 12/2015 |
| WO | 2015196194 A1 | 12/2015 |
| WO | 2017070372 A1 | 4/2017 |
| WO | 2019094365 A1 | 5/2019 |
| WO | 2019094365 A9 | 12/2019 |
| WO | 2020264214 A1 | 12/2020 |

OTHER PUBLICATIONS

ISR issued in international application No. PCT/US2022/014004, mailed on May 11, 2022.
Uknown, Omniergy Power Glory Battery Tech (HK) Co., Ltd., Spefication for Lithium Battery Model CR2032, http:www.omenry.com.hk, 9 pages, last downloaded May 10, 2022.
Unknown, Data Sheet, Lithium Manganese Dioxide Battery, CR2032, Maxell, Hitachi Maxell, Ltd., Nov. 2008.

(56) References Cited

OTHER PUBLICATIONS

Unknown, Manganese Dioixide Lithium Coin Batteries: Individual Specifications, CR2032 and CR2330, Panasonic, Aug. 2005.
Unknown, Product DataSheet, Energizer CR2032, Lithium Coin, Form No. 2032NA0618, 1 page, last downloaded May 10, 2022.
Unknown, S132 SoftDevice Specification v6.1, Nordic Semiconductor, Aug. 23, 2018, 114 p.
Unknown, The Swiss Power Source, Renata batteries, 3V Lithium Batteries, Engineering Specifications for Renata 3V Lithium Button Cells (MNO2/Li), Dec. 2010.
History-Computer (HC). "What is a Real-Time Clock (RTC) and Why are They Important in Computing?" (Year: 2022).
Hoffman.; High Pulse Drain Impact on CR2032 Coin Cell Battery Capacity; 2011; Nordic Semiconductor.
International Preliminary Report on Patentability issued May 17, 2022 for PCT/US2020/65235.
Extended European Search Report for European Application No. 20902088.2 dated Aug. 3, 2023.

\* cited by examiner

| Frequency \ Duration | 1 | 5 | 10 | 20 | 30 | 50 |
|---|---|---|---|---|---|---|
| 1 | 1 | 5 | 10 | 20 | 30 | 50 |
| 5 | 5 | 25 | 50 | 100 | 150 | 250 |
| 20 | 20 | 100 | 200 | 400 | 600 | 1000 |
| 50 | 50 | 250 | 500 | 1000 | 1500 | 2500 |
| 100 | 100 | 500 | 1000 | 2000 | 3000 | 5000 |
| 150 | 150 | 750 | 1500 | 3000 | 4500 | 7500 |

Fig. 10

Obverse    Reverse

[A]    [B]    [C]

NON-INVASIVE NERVE STIMULATOR WITH BATTERY MANAGEMENT

CROSS REFERENCE TO RELATED APPLICATIONS

This application claims priority to U.S. Provisional Patent Application Ser. No. 63/142,362, filed on Jan. 27, 2021, the disclosure of which is hereby incorporated by reference.

FIELD

This invention pertains to the stimulation of nerves by topical stimulators to control or influence muscles, tissues, organs, or sensation, including pain, in mammals, including humans.

BACKGROUND INFORMATION

Nerve disorders may result in loss of control of muscle and other body functions, loss of sensation, or pain. Surgical procedures and medications sometimes treat these disorders but have limitations. This invention pertains to a system for offering other options for treatment and improvement of function.

BRIEF DESCRIPTION OF THE DRAWINGS

FIG. 10 is a table relating charge duration vs. frequency to provide feedback to the adaptive protocol in accordance with one example.

DETAILED DESCRIPTION

A non-invasive nerve stimulator/activator in accordance with various examples disclosed herein includes novel circuitry to adequately boost voltage to a required level and to maintain a substantially constant level of charge for nerve activation while maximizing battery life. Further, a feedback loop provides for an automatic determination and adaptation of the applied charge level.

The nerve stimulator disclosed herein, in the form of a patch, can cause the stored battery voltage to be drained upon initiation of a stimulation charge due to a spike in voltage demand. Therefore, example inventions use the novel circuitry to draw battery power in stages using capacitors to store charge until the charge level reaches its set level for discharge.

Figure 1:
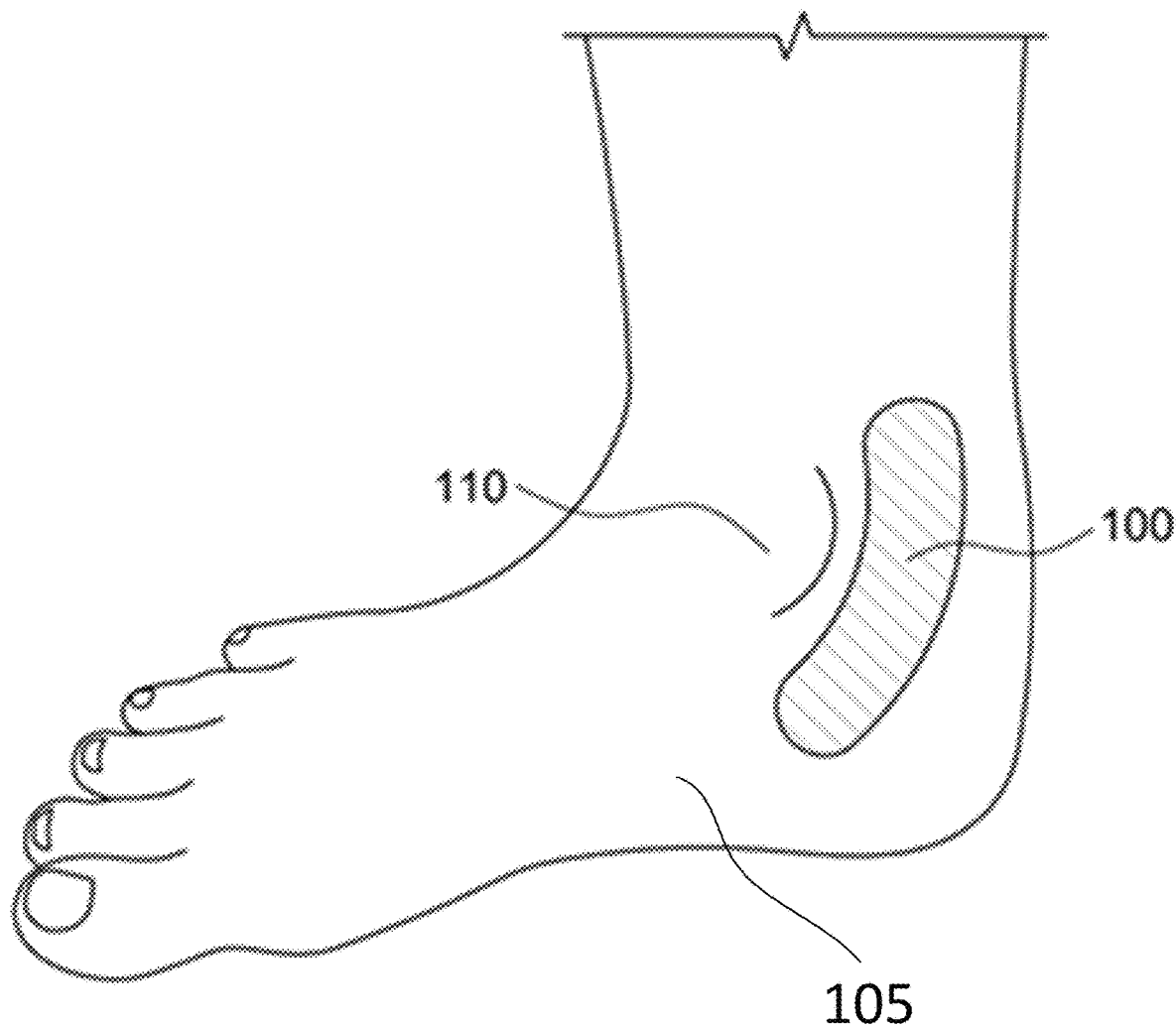
FIG. 1 illustrates an example patch that is affixed to a location behind an ankle bone of a user.

FIG. 1 illustrates an example patch 100, also referred to as a smart band aid or smartpad or Topical Nerve Activator ("TNA") or topical nerve activation patch, that is affixed to a location behind an ankle bone 110 of a user 105. In the example of FIG. 1, patch 100 is adapted to activate/stimulate the tibial nerve of user 105 and can have one shape for the left ankle and a similar but mirrored shape for the right ankle. In other examples, patch 100 is worn at different locations of user 105 to activate the tibial nerve from a different location, or to activate a different nerve of user 105.

Patch 100 is used to stimulate these nerves and is convenient, unobtrusive, self-powered, and may be controlled from a smartphone or other control device. This has the advantage of being non-invasive, controlled by consumers themselves, and potentially distributed over the counter without a prescription. Patch 100 provides a means of stimulating nerves without penetrating the dermis, and can be applied to the surface of the dermis at a location appropriate for the nerves of interest. In examples, patch 100 is applied by the user and is disposable.

Patch 100 in examples can be any type of device that can be fixedly attached to a user, using adhesive in some examples, and includes a processor/controller and instructions that are executed by the processor, or a hardware implementation without software instructions, as well as electrodes that apply an electrical stimulation to the surface of the user's skin, and associated electrical circuitry. Patch 100 in one example provides topical nerve activation/stimulation on the user to provide benefits to the user, such as bladder management for an overactive bladder ("OAB"), or for relief from obstructive sleep apnea ("OSA").

Patch 100 in one example can include a flexible substrate, a malleable dermis conforming bottom surface of the substrate including adhesive and adapted to contact the dermis, a flexible top outer surface of the substrate approximately parallel to the bottom surface, a plurality of electrodes positioned on the patch proximal to the bottom surface and located beneath the top outer surface and directly contacting the flexible substrate, electronic circuitry (as disclosed herein) embedded in the patch and located beneath the top outer surface and integrated as a system on a chip that is directly contacting the flexible substrate, the electronic circuitry integrated as a system on a chip and including an electrical signal generator integral to the malleable dermis conforming bottom surface configured to electrically activate the one or more electrodes, a signal activator coupled to the electrical signal generator, a nerve stimulation sensor that provides feedback in response to a stimulation of one or more nerves, an antenna configured to communicate with a remote activation device, a power source in electrical communication with the electrical signal generator, and the signal activator, where the signal activator is configured to activate in response to receipt of a communication with the activation device by the antenna and the electrical signal generator configured to generate one or more electrical stimuli in response to activation by the signal activator, and the electrical stimuli configured to stimulate one or more nerves of a user wearing patch 100 at least at one location proximate to patch 100. Additional details of examples of patch 100 beyond the novel details disclosed herein are disclosed in U.S. Pat. No. 10,016,600, entitled "Topical Neurological Stimulation", the disclosure of which is hereby incorporated by reference.

Figure 2:
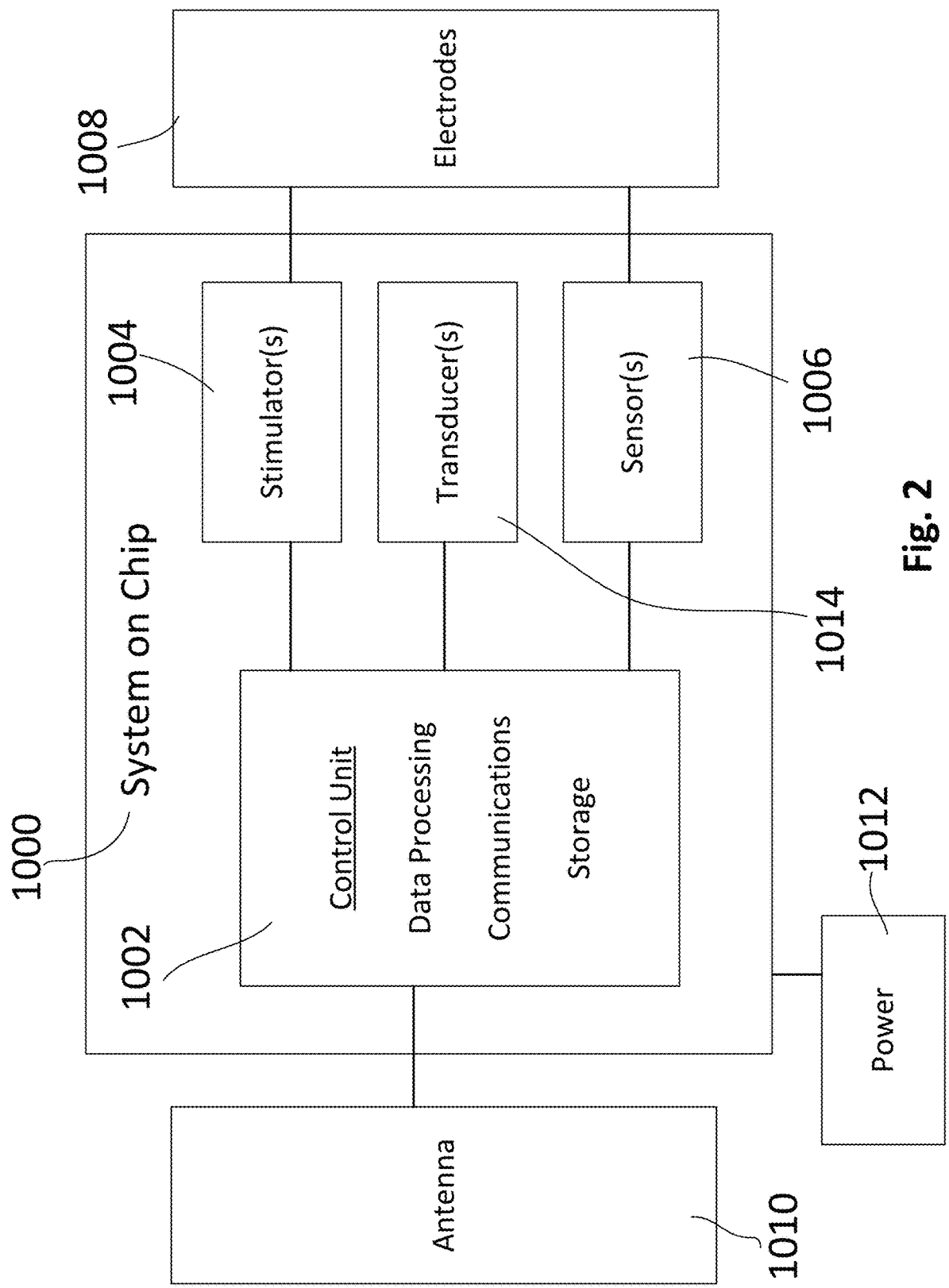
FIG. 2 is a block diagram illustrating hardware/software related elements of an example of the patch of FIG. 1.

FIG. 2 is a block diagram illustrating hardware/software related elements of an example of patch 100 of FIG. 1. Patch 100 includes electronic circuits or chips 1000 that perform the functions of: communications with an external control device, such as a smartphone or fob (which can communicate with patch 100 using wireless communication, such as Bluetooth Low Energy ("BLE")), or external processing such as cloud based processing devices, nerve activation via electrodes 1008 that produce a wide range of electric fields according to a treatment regimen, and a wide range of sensors 1006 such as, but not limited to, mechanical motion and pressure, temperature, humidity, acoustic, chemical and positioning sensors. In another example, patch 100 includes transducers 1014 to transmit signals to the tissue or to receive signals from the tissue.

One arrangement is to integrate a wide variety of these functions into a system on a chip 1000. Within this is shown a control unit 1002 for data processing, communications, transducer interface and storage, and one or more stimulators 1004 and sensors 1006 that are connected to electrodes 1008. Control unit 1002 can be implemented by a general purpose processor/controller, or a specific purpose processor/controller, or a special purpose logical circuit. An antenna 1010 is incorporated for external communications by control unit 1002. Also included is an internal power supply 1012, which may be, for example, a battery. The capacity of the battery may be about 1 mAh to about 100 mAh. Other examples may include an external power supply. It may be necessary to include more than one chip to accommodate a wide range of voltages for data processing and stimulation, or one or more of the functionality may be implemented on its own separate chip/electronic package. Electronic circuits and chips will communicate with each other via conductive tracks within the device capable of transferring data and/or power.

Patch 100 interprets a data stream from control unit 1002 to separate out message headers and delimiters from control instructions. In one example, control instructions include information such as voltage level and pulse pattern. Patch 100 activates stimulator 1004 to generate a stimulation signal to electrodes 1008 placed on the tissue according to the control instructions. In another example, patch 100 activates transducer 1014 to send a signal to the tissue. In another example, control instructions cause information such as voltage level and a pulse pattern to be retrieved from a library stored by patch 100, such as storage within control unit 1002.

Patch 100 receives sensory signals from the tissue and translates them to a data stream that is recognized by control unit 1002. Sensory signals can include electrical, mechanical, acoustic, optical and chemical signals. Sensory signals are received by patch 100 through electrodes 1008 or from other inputs originating from mechanical, acoustic, optical, or chemical transducers. For example, an electrical signal from the tissue is introduced to patch 100 through electrodes 1008, is converted from an analog signal to a digital signal and then inserted into a data stream that is sent through antenna 1010 to the external control device. In another example, an acoustic signal is received by transducer 1014, converted from an analog signal to a digital signal and then inserted into a data stream that is sent through the antenna 1010 to the external control device. In some examples, sensory signals from the tissue are directly interfaced to the external control device for processing.

In examples of patch 100 disclosed above, when being used for therapeutic treatment such as bladder management for OAB, there is a need to control the voltage by boosting the voltage to a selected level and providing the same level of charge upon activation to a mammalian nerve. Further, there is a need to conserve battery life by selectively using battery power. Specifically, it has been observed that stored battery voltage may be drained upon initiation of a stimulation charge due to a spike in voltage demand. In contrast, patch 100 includes novel circuitry to draw battery power in stages using capacitors to store charge until the charge level reaches its set level for discharge.

Further, there is a need to create a compact electronics package to facilitate mounting the electronics package on a relatively small mammalian dermal patch in the range of the size of an ordinary adhesive patch or band aid.

To meet the above needs, examples implement a novel boosted voltage circuit that includes a feedback circuit and a charge application circuit. Specifically, patch 100 uses a combination of hardware circuit and firmware code to manage the timing of both charging and discharging a high voltage on a capacitor. A microcontroller is used to run the firmware and provides various peripherals to control and monitor the circuit. Pulse width modulation ("PWM") outputs are used to turn external switches on and off with controlled duty cycles, and to enable the output of the high voltage pulse to the application at a particular time. Analog to digital converters ("ADCs") are used to measure current and voltage, the measurements used to adapt the timings as needed.

Figure 3A:
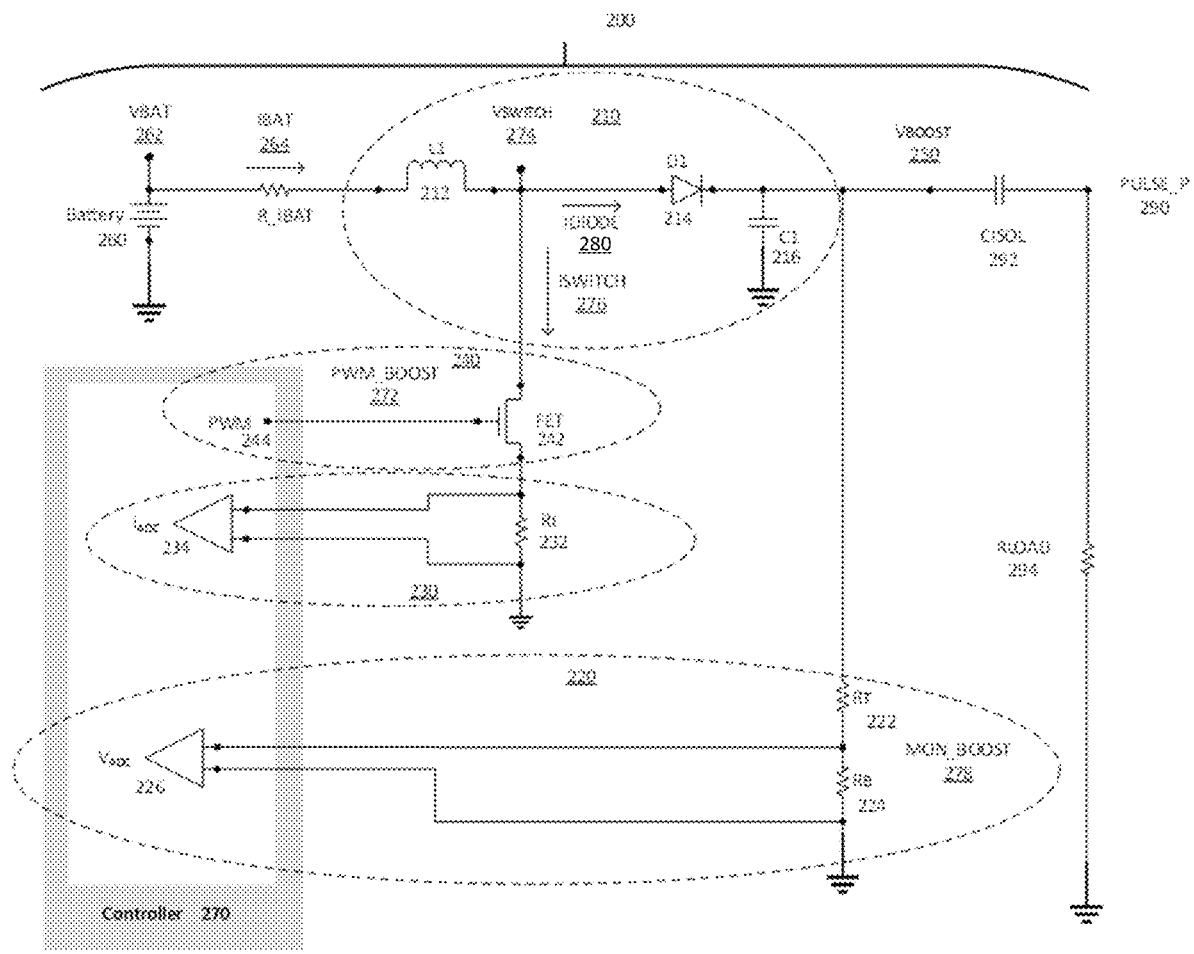
FIG. 3A is a circuit diagram of an example of a boosted voltage circuit that provides feedback.
Figure 3B:
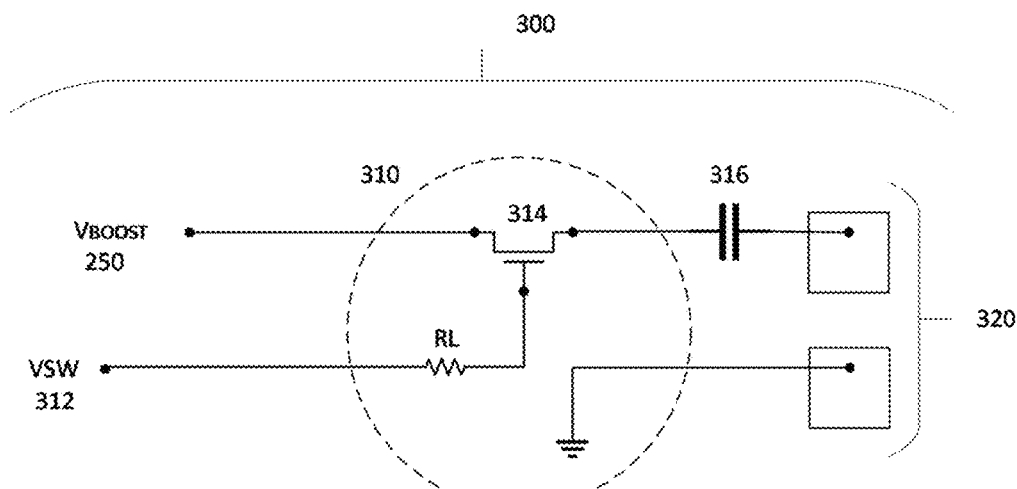
FIG. 3B is a circuit diagram of an example of a charge application circuit that uses an output of the boosted voltage circuit.

FIG. 3A is a circuit diagram of an example of the boosted voltage circuit 200 that provides feedback. FIG. 3B is a circuit diagram of an example of a charge application circuit 300 that uses an output of boosted voltage circuit 200. Boosted voltage circuit 200 includes both electrical components and a controller/processor 270 that includes a sequence of instructions that together modify the voltage level of activation/stimulation delivered to the external dermis of user 105 by patch 100 through electrodes. Controller/processor 270 in examples is implemented by control unit 1002 of FIG. 2.

Boosted voltage circuit 200 can replace an independent analog-controlled boost regulator by using a digital control loop to create a regulated voltage, output voltage 250, from the battery source. Output voltage 250 is provided as an input voltage to charge application circuit 300. In examples, this voltage provides nerve stimulation currents through the dermis/skin to deliver therapy for an overactive bladder or other maladies. Output voltage 250, or "VBoost", at voltage output node 250 (i.e., the high voltage accumulated at capacitor 216), uses two digital feedback paths 220, 230, through controller 270. In each of these paths, controller 270 uses sequences of instructions to interpret the measured voltages at voltage monitor 226, or "$V_{ADC}$" (measured using a voltage divider of two resistors) and current monitor 234, or "$I_{ADC}$" (measured across a small resistor), and determines the proper output control for accurate and stable output voltage 250.

Boosted voltage circuit 200 includes an inductor 212, a diode 214, and a capacitor 216 that together implement a boosted converter circuit 210. A voltage monitoring circuit 220 includes a resistor divider formed by a top resistor 222, or "RT", a bottom resistor 224, or "RB" and voltage monitor 226. A current monitoring circuit 230 includes a current measuring resistor 232, or "RI" and current monitor 234. A pulse width modulation ("PWM") circuit 240 includes a field-effect transistor ("FET") switch 242, and a PWM driver 244. Output voltage 250 functions as a sink for the electrical energy. A battery 260, and corresponding input voltage 262, or "$V_{BAT}$", is the source for the electrical energy, and can be implemented by power 1012 of FIG. 2. Circuit 200 further includes a capacitor (CISOL) 292 and a load impedance ("RLOAD") 294.

PWM circuit 240 alters the "on" time within a digital square wave, fixed frequency signal to change the ratio of time that a power switch is commanded to be "on" versus "off." In boosted voltage circuit 200, PWM driver 244 drives FET switch 242 to "on" and "off" states.

In operation, controller 270 turns on the switch, FET 242, using PWM output 244, with signal PWM_BOOST 272 (i.e., the output of PWM 244). Controller 270 measures the current through FET 242 using current measuring resistor 232 and current monitor 234, as signal ISWITCH 274. Controller 270 measures the voltage VBOOST 250 through the pair of resistors, RT 222 and RS 224, and Voltage ADC 226.

Battery current, IBAT 264, is measured across a small resistor ("R_IBAT") Both the battery current measurement IBAT 264 and the battery voltage measurement VBAT 262 use additional ADCs implemented by controller 270, not shown.

The energy delivered for an application pulse from VBOOST 250 is conducted through inductor 212 and diode 214 to charge boost capacitor 216. The current IDIODE 280 (i.e., the current flowing through diode 214), which charges boost capacitor 216, is calculated as the difference between IBAT 264 and the switch current ISWITCH 276 (i.e., the current flowing through charging switch FET 242).

In an example, the boost circuit contains one stage to achieve the higher voltage. In an example, the boost circuit contains multiple stages to help with generating high voltages, and may include a voltage doubler as an additional stage, disclosed in detail below.

In an example, the current and voltage measurements shown using two ADCs 226, 234 are measured using a single ADC with a switch to select one or the other input path.

In operation, PWM_VBOOST 272 is high for a brief period to momentarily turn on the FET 242. The pulse width of PWM_VBOOST 272 is controlled by PWM 244, which is itself controlled by firmware in controller 270. This short enabling pulse allows current, IBAT 264, to flow through inductor 212. Due to the inductance and capacitance of the circuit, voltage VSWITCH 274 is a transient higher voltage than the output voltage of the battery 260, VBAT 262. VSWITCH 274 delivers current DIODE 280 into the one-, or two-, or more stage voltage boost circuit. The current DIODE 280 cannot flow back through the diodes, so it charges boost capacitor 216 a bit more each time DIODE 280 flows during the time VSWITCH 274 is high.

VBOOST 250 is monitored actively by MON_VBOOST 278. This monitored voltage is sensed by controller 270 and used in a firmware feedback loop to control the enable time of the PWM output. Therefore, the amplitude of VBOOST 250 is controlled dynamically when the total charge time for VBOOST 250 or the target voltage value of VBOOST 250 changes, such as due to changes in resistor R_LOAD 294. PULSE_P 290 is the voltage applied to the electrodes which in turn work through R_LOAD 294 to deliver an application pulse.

In an example, the PWM, which runs at 400 KHz, has a period of 2.5 microseconds ("μs"). Controller 270 monitors VBOOST 250 repeatedly, using ADC 226 with measurement time of 11 μs. The number of ADC measurements made at a constant PWM duty cycle is set by the firmware, thus limiting the current at that stage of the ramp up of VBOOST. In the example, 240 ADC measurements are made at 11 μs, for a "step" time of approximately 2.4 milliseconds.

In operation, when FET switch 242 is on (i.e., conducting), the drain of FET switch 242 is brought down to Ground/GND or ground node 270. FET switch 242 remains on until its current reaches a level selected by controller 270 acting as a servo controller. This current is measured as a representative voltage on current measuring resistor 232 detected by current monitor 234. Due to the inductance of inductor 212, energy is stored in the magnetic field within inductor 212. The current flows through current measuring resistor 232 to ground until FET switch 242 is opened by PWM driver 244.

When the intended pulse width duration is achieved, controller 270 turns off FET switch 242. The current in inductor 212 reroutes from FET switch 242 to diode 214, causing diode 214 to forward current. Diode 214 charges capacitor 216. Therefore, the voltage level at capacitor 216 is controlled by controller 270.

Output voltage 250 is controlled using an outer servo loop of voltage monitor 226 and controller 270. Output voltage 250 is measured by the resistor divider using top resistor 222, bottom resistor 224, and voltage monitor 226. The values of top resistor 222 and bottom resistor 224 are selected to keep the voltage across bottom resistor 224 within the monitoring range of voltage monitor 226. Controller 270 monitors the output value from voltage monitor 226.

Charge application circuit 300 includes a pulse application circuit 310 that includes an enable switch 314. Controller 270 does not allow enable switch 314 to turn on unless output voltage 250 is within a desired upper and lower range of the desired value of output voltage 250. Pulse application circuit 310 is operated by controller 270 by asserting an enable signal/voltage 312, or "VSW", which turns on enable switch 314 to pass the electrical energy represented by output voltage 250 through electrodes 320 via a capacitor 316. Capacitor 316 isolates electrodes 320 from DC voltages in the charging circuit, as a safety feature in the device. At the same time, controller 270 continues to monitor output voltage 250 and controls PWM driver 244 to switch FET switch 242 on and off and to maintain capacitor 216 to the desired value of output voltage 250.

The stability of output voltage 250 can be increased by an optional inner feedback loop through FET Switch 242, current measuring resistor 232, and current monitor 234. Controller 270 monitors the output value from current monitor 234 at a faster rate than the monitoring on voltage monitor 226 so that the variations in the voltages achieved at the cathode of diode 214 are minimized, thereby improving control of the voltage swing and load sensitivity of output voltage 250.

As described, in examples, controller 270 can use multiple feedback loops to adjust the duty cycle of PWM driver 244 to create a stable output voltage 250 across a range of values. Controller 270 uses multiple feedback loops and monitoring circuit parameters to control output voltage 250 and to evaluate a proper function of the hardware. Controller 270 acts on the feedback and monitoring values in order to provide improved patient safety and reduced electrical hazard by disabling incorrect electrical functions.

In some examples, controller 270 implements the monitoring instructions in firmware or software code. In some examples, controller 270 implements the monitoring instructions in a hardware state machine.

In some examples, voltage monitor 226 is an internal feature of controller 270. In some examples, voltage monitor 226 is an external component, which delivers its digital output value to a digital input port of controller 270.

In some examples, current monitor 234 is an internal feature of controller 270. In some examples, current monitor 234 is an external component, which delivers its digital output value to a digital input port of controller 270.

An advantage of boosted voltage circuit 200 over known circuits is decreased component count which may result in reduced costs, reduced circuit board size and higher reliability. Further, boosted voltage circuit 200 provides for centralized processing of all feedback data which leads to faster response to malfunctions. Further, boosted voltage circuit 200 controls outflow current from $V_{BAT}$ 260, which increases the battery's lifetime and reliability.

Figure 4:
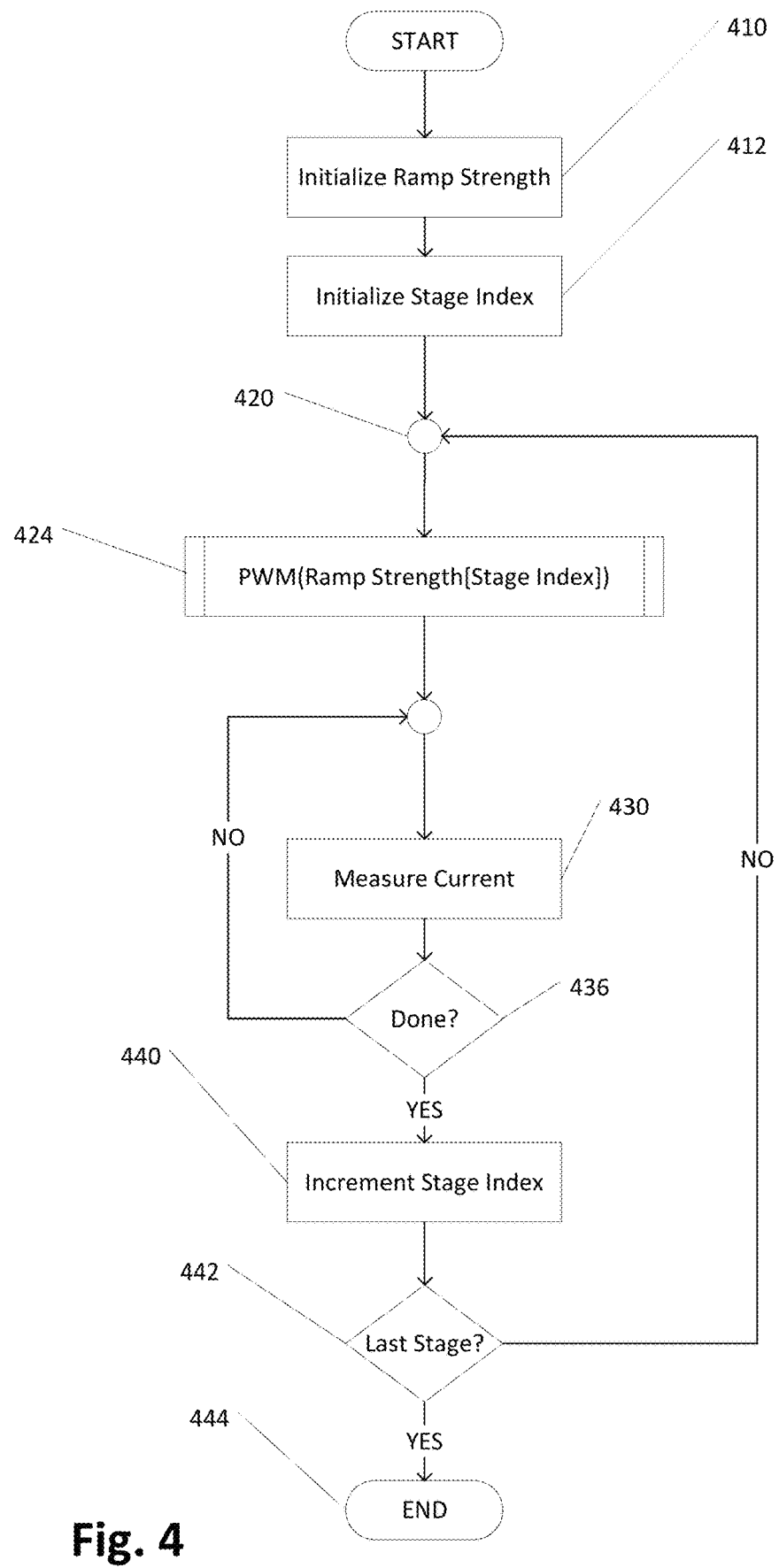
FIG. 4 is a flow diagram of the functionality of the controller for monitoring and controlling the output voltage, including its ramp rate.

FIG. 4 is a flow diagram of the functionality of controller 270 for monitoring and controlling output voltage 250, including its ramp rate. In one example, the functionality of the flow diagram of FIG. 4 (and FIGS. 8, 11 and 12 below) is implemented by software stored in memory or other computer readable or tangible medium, and executed by a processor. In other examples, the functionality may be performed by hardware (e.g., through the use of an application-specific integrated circuit ("ASIC"), a programmable gate array ("PGA"), a field programmable gate array ("FPGA"), etc.), or any combination of hardware and software.

The pulse width modulation of FET switch 242 is controlled by one or more pulses for which the setting of each pulse width allows more or less charge to accumulate as a voltage at capacitor 216 through diode 214. This pulse width setting is referred to as the ramp strength and it is initialized at 410. Controller 270 enables each pulse group in sequence with a pre-determined pulse width, one stage at a time, using a stage index that is initialized at 412. The desired ramp strength is converted to a pulse width at 424, which enables and disables FET switch 242 according to the pulse width. During the intervals when FET switch 242 is "on", the current is measured by current monitor 234 at 430 and checked against the expected value at 436. When the current reaches the expected value, the stage is complete and the stage index is incremented at 440. If the desired number of stages have been applied 442, then the functionality is complete. Otherwise, the functionality continues to the next stage at 420.

As a result of the functionality of FIG. 4, $V_{BAT}$ 260 used in patch 100 operates for longer periods as the current drawn from the battery ramps at a low rate of increase to reduce the peak current needed to achieve the final voltage level 250 for each activation/stimulation treatment. The PWM 244 duty cycle is adjusted by controller 270 to change the ramp strength at 410 to improve the useful life of the battery.

An open loop protocol to control current to electrodes in known neural stimulation devices does not have feedback controls. It commands a voltage to be set, but does not determine the amount of actual current delivered to the user. A stimulation pulse is sent based on preset parameters and generally cannot be modified based on feedback from the patient's anatomy. When the device is removed and repositioned, the electrode placement varies. Also the humidity and temperature of the anatomy changes throughout the day. All these factors affect the actual charge delivery if the voltage is preset. Charge control is a patient safety feature and facilitates an improvement in patient comfort, treatment consistency and efficacy of treatment.

In contrast, examples of patch 100 includes features that address these shortcomings using controller 270 to regulate the charge applied by electrodes 320. Controller 270 samples the voltage of the stimulation waveform, providing feedback and impedance calculations for an adaptive protocol to modify the stimulation waveform in real time. The current delivered to the anatomy by the stimulation waveform is integrated using a differential integrator and sampled and then summed to determine the actual charge delivered to the user for a treatment, such as OAB treatment. After every pulse in a stimulation event, this data is analyzed and used to modify, in real time, subsequent pulses.

This hardware adaptation allows a firmware protocol to implement an adaptive protocol, disclosed in detail below. This protocol regulates the charge applied to the body by changing output voltage ("$V_{BOOST}$") 250. A treatment is performed by a sequence of periodic pulses, which deliver charge into the body through electrodes 320. Some of the parameters of the treatment are fixed and some are user adjustable. The strength, duration and frequency may be user adjustable. The user may adjust these parameters as necessary for comfort and efficacy. The strength may be lowered if there is discomfort and raised if nothing is felt. The duration can be increased if the maximum acceptable strength results in an ineffective treatment.

Figure 5:
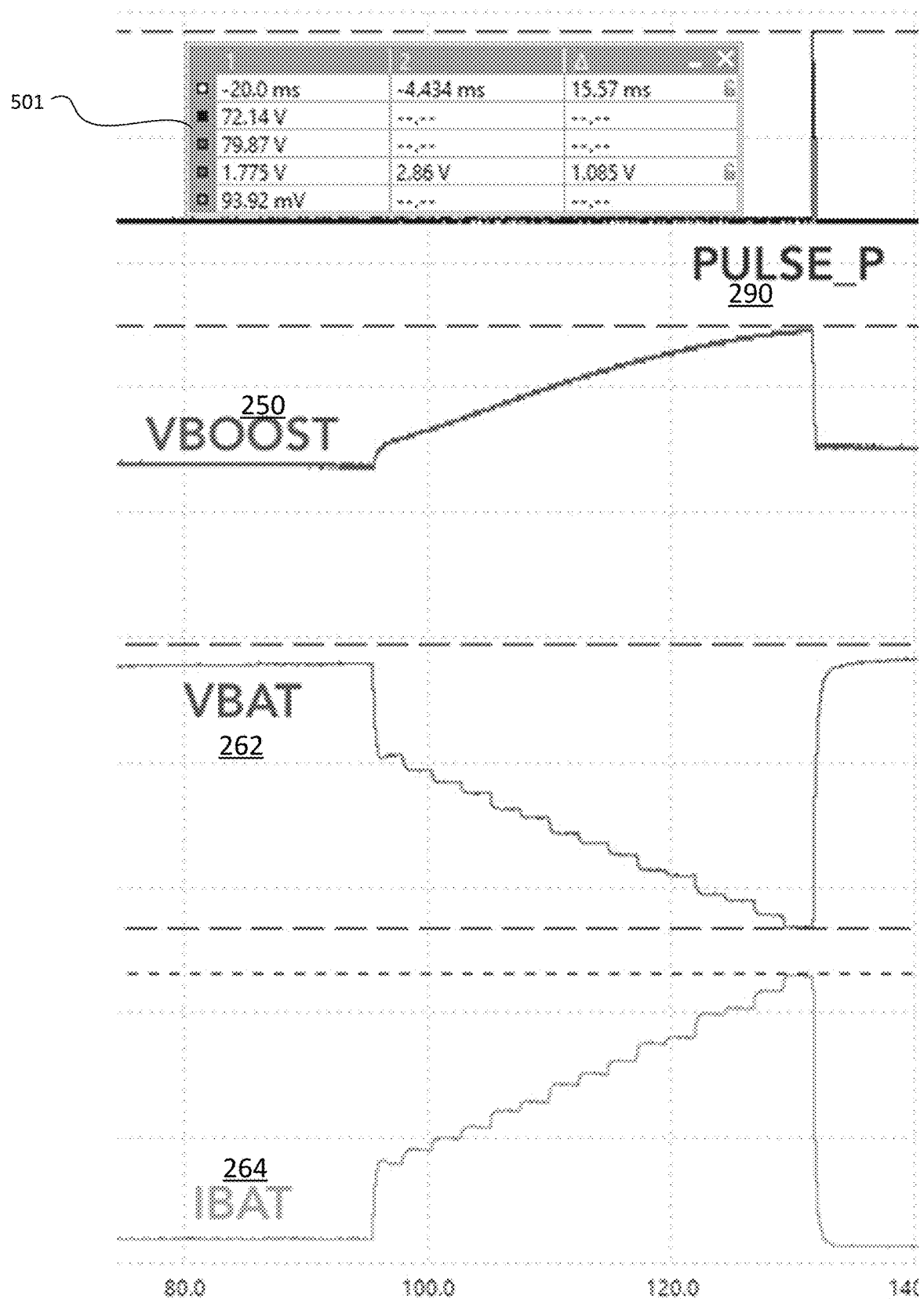
FIG. 5 illustrates four of the principal waveforms for metering battery power using the circuit of FIG. 3A in example inventions.

FIG. 5 illustrates four of the principal waveforms for metering battery power using circuit 200 of FIG. 3A in example inventions. The top trace, PULSE_P 290, is the voltage applied to the electrodes, which in turn work through R_LOAD 294 to deliver an application pulse. The second trace, VBOOST 250, is the voltage accumulated at boost capacitor CBOOST 216. The third trace is the voltage at battery 260, VBAT 262. The fourth trace is the current from battery 260, IBAT 264. Table 501 shows the values of these signals, which are scaled by the values of resistors in circuit 200.

Figure 6:
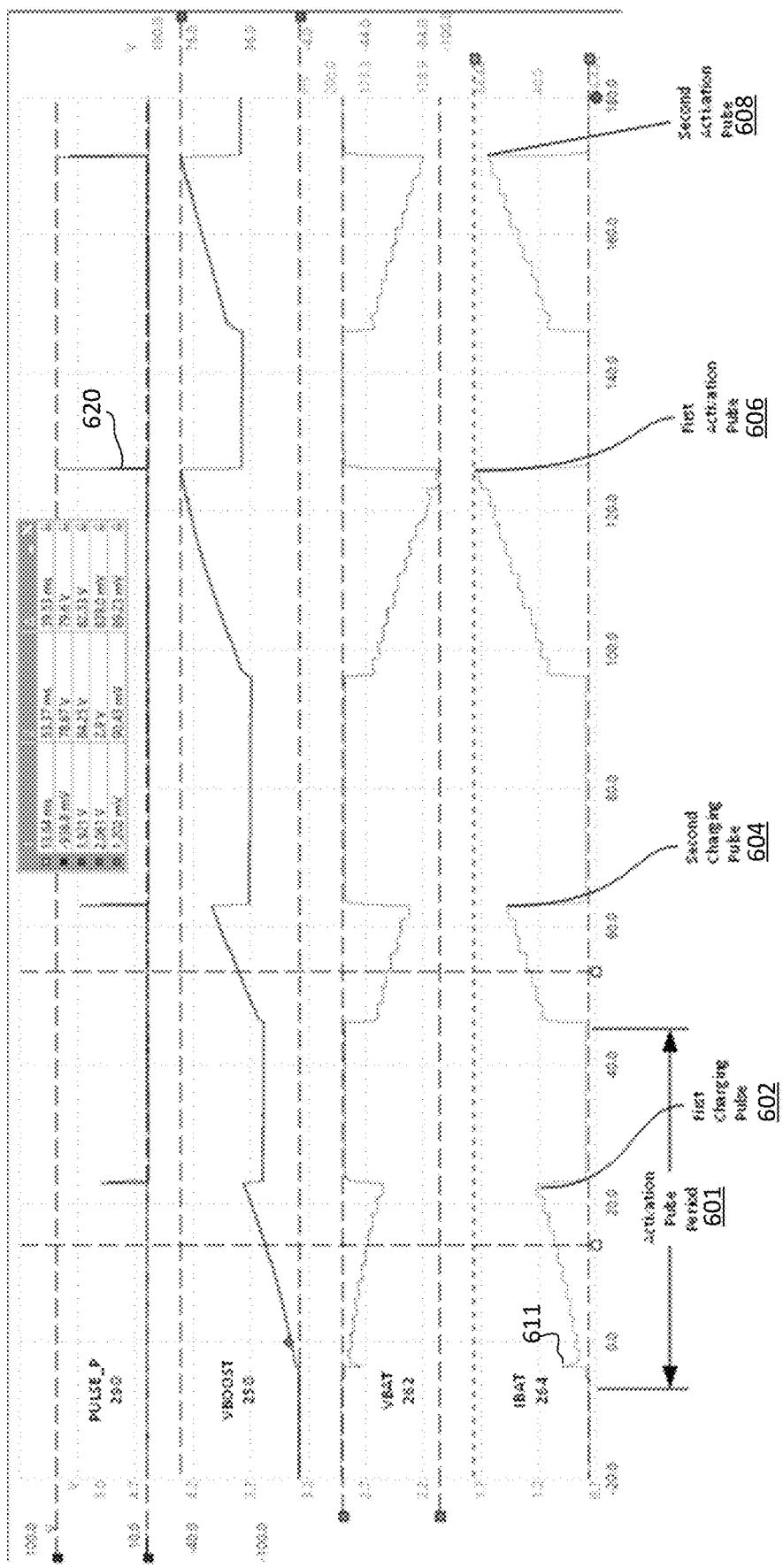
FIG. 6 illustrates waveforms showing how a treatment period is started utilizing the circuitry of FIGS. 3A and 3B in example inventions.

FIG. 6 illustrates waveforms showing how a treatment period is started utilizing the circuitry of FIGS. 3A and 3B in example inventions. The "treatment period" is the overall time during which patch 100 applies the sequence of treatment pulses to the user. If the PWM protocol charges boost capacitor CBOOST 216 all the way up to the application voltage on a single ramp, one or more of three results may occur. First, battery 260 may fail to deliver the necessary energy and an activation pulse may be impossible to deliver. Second, battery output voltage, VBAT 262, may be pulled so low due to the current, IBAT 264, and the internal source resistance of battery 260 that VBAT 262 falls below the minimum needed for operation of the components in circuit 200. Controller 270 and/or other components may cease to operate and patch 100 may therefore fail to operate. Third, in cases when the activation voltage is achieved and the circuitry does not fail, the rapid demand for energy from battery 260 may shorten the life of battery 260 and reduce the useable energy from battery 260 to much less than its specified capacity. In contrast, example inventions use multiple activation periods before capacitor 216 is charged to the application voltage.

FIG. 6 includes a first charging pulse 602, a second charging pulse 604, a first activation pulse 606 and a second activation pulse 608.

In one example, controller 270 may specify a minimum power supply level of 1.8 V. In the example of FIG. 6, the average IBAT current is 92 mA during the charge time for the fourth pulse along the timeline (i.e., second activation pulse 608). The current multiplied by the duration is equal to the charge per pulse. In this example, 92 mA×50 msec× 4000 pulses is equal to 17.6 Coulombs. The energy drawn from battery 260 through 40 treatments should be only 23% of the specified battery energy (17.6 divided by 756 Coulombs), but battery 260 may be exhausted before the 40 treatments have been applied to the load using known circuit solutions. This poor efficiency is due to the high peak currents drawn from battery 260, for which its chemistry cannot keep pace.

FIG. 6 shows in first pulse 602 on VBOOST 250 that the voltage is raised to approximately 50% of the target VBOOST voltage, or approximately 40V. The PWM duty cycle and pulse count use the time allotted in the activation period 601 to reach this 50% voltage while keeping the current demanded from battery 260 within a maximum limit. The "activation period" is the time from one treatment pulse to the next treatment pulse. Partially charging Boost Capacitor 216 uses one activation period out of the sequence of activation periods in a treatment period without delivering an effective PULSE_P 290 to the user, but this partial charge improves the efficiency of battery energy usage such that battery 260 can deliver more complete treatments when compared to a protocol which drives VBOOST 250 to its target value more quickly, such as within one activation period. As shown, examples include a voltage spike 611 at the leading edge of first charging pulse 602. This spike is due to the current surge into inductor 212. The amplitude of spike 611 is limited to an acceptable voltage by the pulse width of the PWM during this first charging pulse 602. A wider PWM pulse would create a larger and possibly damaging voltage spike.

In an example invention, the activation period is 50 msec, or a rate of 20 Hz, and the treatment period is 10 seconds, for a total of 200 activation periods.

FIG. 6 shows in the second pulse 604 on VBOOST 250 that the voltage is raised from 40V to about 60V. If the second pulse were to raise VBOOST 250 to its final value (i.e., approximately 80V), there would be another voltage spike at the leading edge of second pulse 604. Since VBOOST 250 is starting at a higher voltage, this second voltage spike might have amplitude greater than the maximum allowed in circuit 200. Therefore, the final VBOOST voltage is approached using two charging pulses, one at approximately 50% of the final voltage and one at approximately 75% of the final voltage in the example.

Different levels of apportioning the charging to the first few pulses of a treatment cycle is possible. The "treatment cycle" is the sum of the treatment period plus any added time to prepare the circuitry for the first treatment pulse.

FIG. 6 further shows in the third pulse 606 and fourth pulse 608 on VBOOST 250 that the voltage has charged to the target value (i.e., approximately 80V). Pulses from the fourth onward to the end of the treatment period all proceed at the target voltage value, provided battery 260 can continue to deliver adequate energy.

Table 501 of FIG. 5 shows that PULSE_P 290 reaches a maximum of 72 volts, corresponding to the target VBOOST voltage as set by the user. VBOOST 250 reaches a maximum of 79 volts. During the charging time of VBOOST 250, VBAT 262 decreases from 2.86 volts to 1.08 volts. The pull-down on VBAT is the result of the increase, step by step, of IBAT 264, which reaches a maximum of 182 mA (the measured voltage for IBAT 264 is across a 0.5 Ohm resistor; thus, according to I=V/R, the current is two times the measured voltage).

Figure 7:
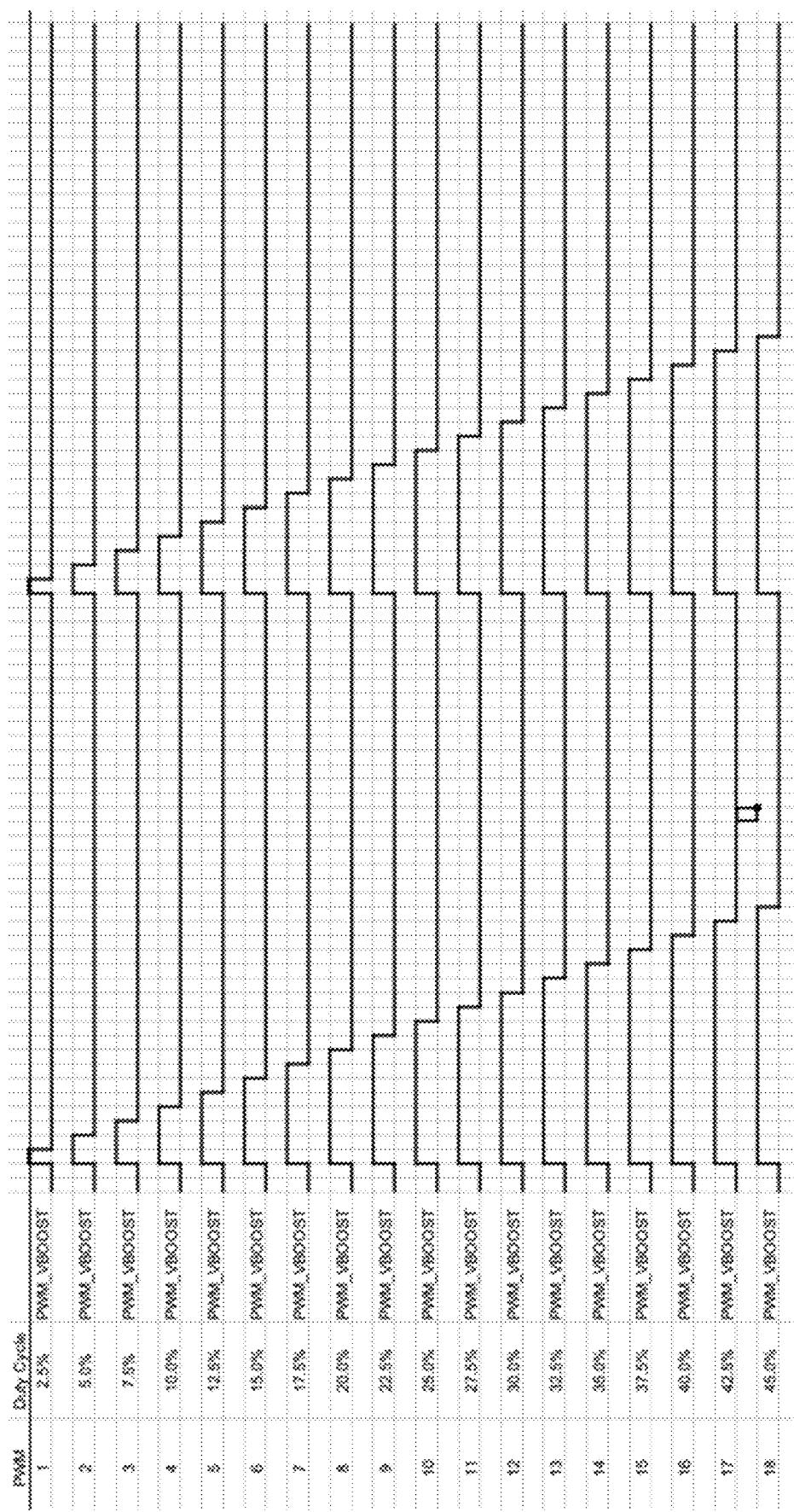
FIG. 7 illustrates example PWM pulse width programming in accordance to example invention.

FIG. 7 illustrates example PWM pulse width programming in accordance to example invention. As shown in FIG. 7, the PWM duty cycles vary from 2.5% to 45%. Using an oscillator of 400 KHz, the PWM period is 2.5 µs. The steps along the curve of the VBAT 262 and IBAT 264 waveforms in FIG. 6 are due to the change in PWM duty cycle. Initially, the PWM uses a low duty cycle. This pulls a DC load through inductor 212 and the battery internal source resistance for only a small part of the PWM period. The low duty cycle minimizes the short-term average IBAT 264, and allows battery 260 time to recover its internal available charge. Although not shown in FIG. 7, some example inventions use up to a 75% duty cycle to achieve a 90V VBOOST 250. In general, the higher the desired VBOOST 250, the higher the PWM duty cycle. Example inventions ramp up duty cycle until VBOOST 250 reaches the desired strength level.

Each time the PWM causes current to be drawn from battery 260, the battery voltage VBAT 262 drops. This is primarily due to the increase in internal source resistance in battery 260, which is a function of its chemistry. To deliver the same amount of charge, and thus increment the output VBOOST 250 in equal steps, battery 260 delivers a larger current IBAT 264 in each PWM step, with the product of VBAT and IBAT proportional to the delivered power.

Other frequencies and PWM duty cycles may be used to ramp the voltage. Steps for increasing VBOOST 250 may be programmed in a linearly increasing voltage, or in other progressive steps such as along a curve.

As shown, in the example of FIG. 6, a treatment pulse 290 is issued after the first and second charging pulse. Since VBOOST 250 is not up to full strength after each of the partial charging pulses, in another example, the firmware in controller 270 will not issue a signal to enable output of the treatment pulse during the partial charging pulse periods. Only when VBOOST 250 is up to full strength will the signal cause a treatment pulse to be sent through R_LOAD 294.

In an example, a pulse is sent to the electrodes during one of the partial charging pulse periods, for the purpose of measuring R_LOAD 294, which may vary from one use to another use. This pulse is not a sufficiently high voltage to be an effective treatment pulse, but indicates to the ADC or ADCs 226 the value of R_LOAD.

In an example, a pulse is sent to the electrodes during two or more of the partial charging pulse periods, for the purpose of measuring R_LOAD 294.

In an example, the partial charging pulse period is different from the activation period, each controlled by controller 270. During the partial charging period (i.e., the time during which charge is drawn from battery 260, through the voltage boost circuit 210, to charge the capacitor CBOOST 216), the time is set to draw energy from battery 260 as long as possible while not exceeding the IBAT 264 allowed from battery 260 and not drawing VBAT 262 too low yet raising the voltage toward the final VBOOST 250 as quickly as possible. Two or more partial charging periods may be required, these being timed prior to the start of the treatment period.

The VBOOST 250 pulse discharges only part of the energy stored in C_BOOST 216. The pulse width of PULSE_P 290 and the load R_LOAD 294 determine the degree to which C_BOOST 216 is discharged. If the timing of the pulse is wider, then more energy is discharged. If the load is a lower than R_LOAD 294, then more energy is discharged. A "discharge period" is the time during which charge is drawn from the capacitor CBOOST 216 and flows as a current through the load impedance, R_LOAD 294, via the electrodes as a treatment pulse.

After the PULSE_P 290 pulse, the circuit needs only to restore VBOOST on C_BOOST 216 to the high voltage needed for the next pulse. Controller 270, using an ADC, measures the voltage on VBOOST after the VBOOST pulse. The firmware calculates how to restore the needed VBOOST, and uses a closed-loop measurement circuit with an ADC (or similar circuit) to monitor the actual VBOOST level.

FIG. 6 further shows that the VBOOST voltage drops to about 40V after the application of the third PULSE_P pulse at 620. Therefore, VBOOST 250 needs to be recharged only from 40V to the target voltage of about 80V, and not from the base voltage before the first application period. Patch 100 keeps the charging current, IBAT 264, within tight limits. This optimizes the rate of energy drawn from battery 260, which allows patch 100 device to use much more of the specified energy capacity of battery 260.

In this example, the PWM is enabled for 2.5 μs 1000 times, creating a 2.5 microsecond step in the waveform of VBAT 262 and IBAT 264. This step size allows the circuit to reach the target VBOOST value in the time allotted, as determined by the period between PULSE_P 290 application pulses. If the desired magnitude of PULSE_P 290 is lower, then fewer steps are needed to charge and recharge VBOOST 250. When the repetition rate of PULSE_P 250 is higher, with a shorter period, then the step size is shorter.

The ramp of VBOOST 250 is controlled via a closed-loop through the controller 270 firmware, where controller 270 measures MON_VBOOST 278 and determines the necessary next charging step.

During the time the output switch 314 is turned on to enable the VBOOST pulse to pass through R_LOAD 294, the battery voltage VBAT 262 recovers to a higher level as the current drawn from the battery, IBAT 264, returns to zero.

In an example, the application period is too short to allow for recharging of CBOOST 216 to the required voltage VBOOST 250. This case occurs when the frequency of applied treatment pulses is higher, such as 100 Hz. In an example of patch 100, two capacitors are placed in parallel in the circuit, each provided with a charging circuit 210 such as that of FIG. 3A, and each provided with an output switch to the shared electrodes. One of the two capacitors is recharged from battery 260 during one application period while the other capacitor is used to output a treatment pulse. The firmware alternates between the two capacitor channels to be able to deliver the necessary VBOOST pulse during each consecutive application period. Only one of the two switches is enabled at a time, such that the energy from one of the capacitors is partially discharged via its switch into R_LOAD 294.

Oscillator Timing

In example inventions, controller 270 includes a real time clock ("RTC") circuit which is used to measure time intervals, including time between activation pulses, and the width of the activation pulses. The RTC circuit runs continuously on controller 270 to continuously track in real time. However, this continuous operation continuously draws power from the battery.

In other example inventions, the RTC circuit is not used and is set to inoperative mode by firmware in controller 270. The firmware sets timers using the on-chip oscillator, which has a known frequency and can therefore measure a time interval. The firmware clears a counter when patch 100 is connected to the fob or smart controller. The zeroed out time becomes the initial time for subsequent activation events. The firmware adjusts the value of the counter each time the time on the timer elapses, as measured by the on-chip oscillator. The firmware may report counter values to the fob or the smart controller, or both. The fob and the smart controller use the real time clock in their own controllers to calculate a real time value for the activation time by adding a value proportional to the counter value and to the activation period to the real time clock value. This allows the firmware to avoid the use of the on-chip real time clock, which saves power consumption and extends the battery life in patch 100 and further allows the fob or the smart controller to calculate real time markers for activations of patch 100. The markers are useful for analysis of the operation of patch 100. The on-chip oscillator runs continuously, but consumes significantly less power than the on-chip real time clock. In example inventions, controller 270 includes a 32.768 kHz+/−250 ppm RC oscillator. A one second interval is generated when dividing by $2^{15}$.

Adaptive Protocol

Figure 8:
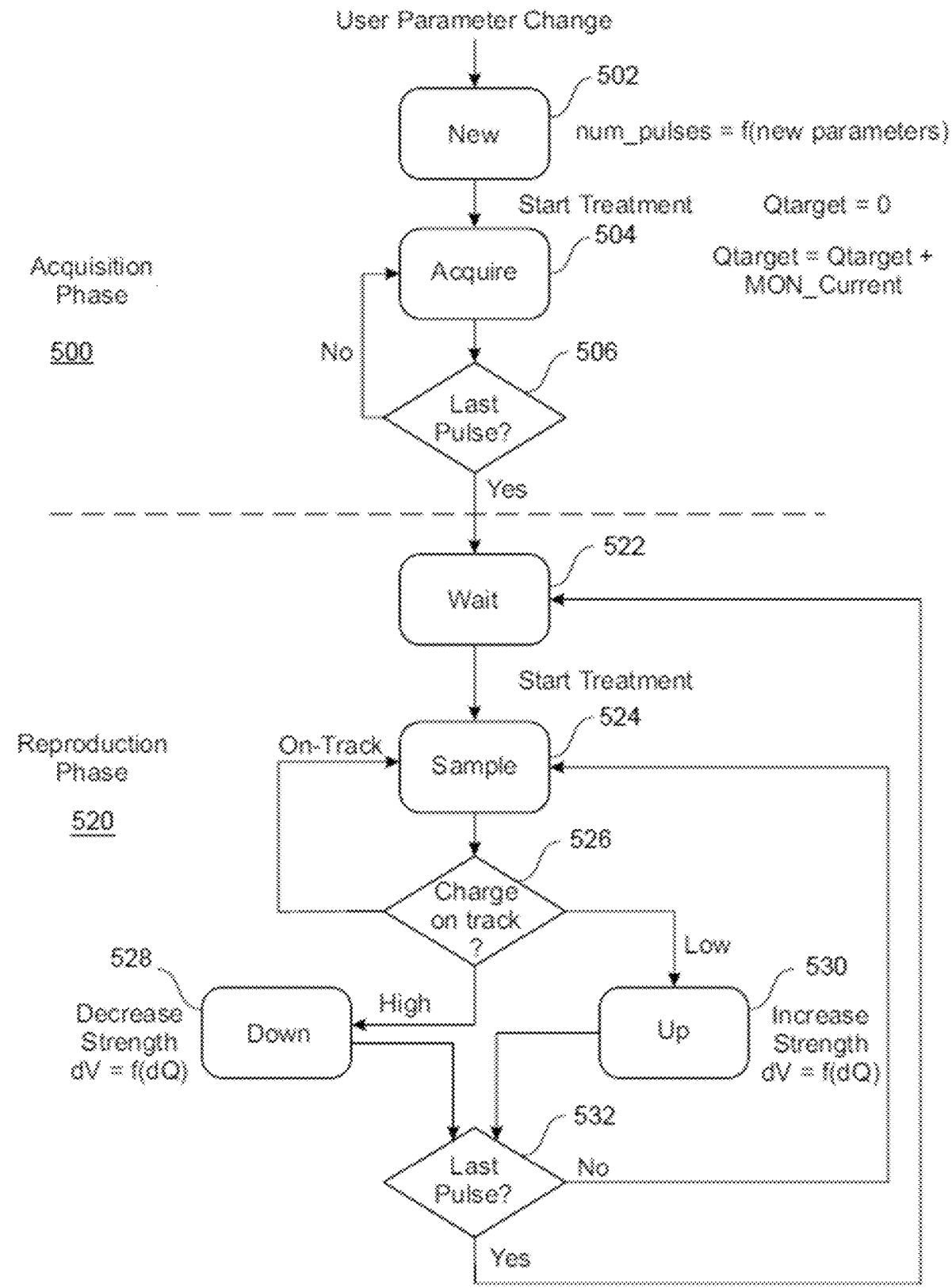
FIG. 8 is a flow diagram in accordance with one example of an adaptive protocol.

A flow diagram in accordance with one example of the adaptive protocol discussed above is shown in FIG. 8. The adaptive protocol strives to repeatedly and reliably deliver a target charge ("$Q_{target}$") in coulombs during a treatment and to account for any environmental changes. Therefore, the functionality of FIG. 8 is to adjust the charge level applied to a user based on feedback, rather than use a constant level.

The mathematical expression of this protocol is as follows:

$Q_{target} = Q_{target}(A*dS + B*dT)$, where $A$ is the Strength
Coefficient—determined empirically, $dS$ is the
user change in Strength, $B$ is the Duration
Coefficient—determined empirically, and $dT$ is
the user change in Duration.

Figure 9:
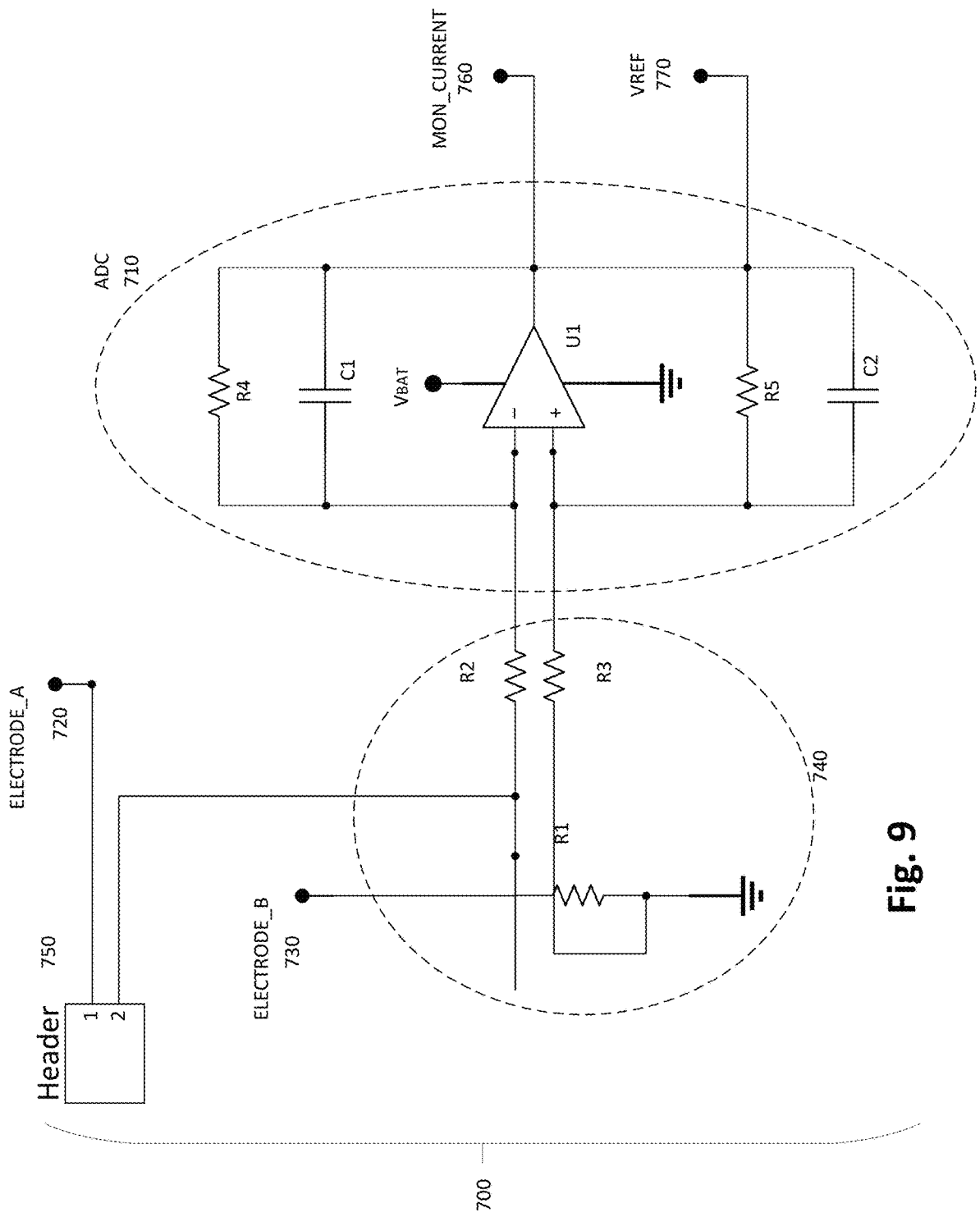
FIG. 9 is a Differential Integrator Circuit used in the adaptive protocol in accordance with one example.

The adaptive protocol includes two phases in one example: Acquisition phase 500 and Reproduction phase 520. Any change in user parameters places the adaptive protocol in the Acquisition phase. When the first treatment is started, a new baseline charge is computed based on the new parameters. At a new acquisition phase at 502, all data from the previous charge application is discarded. In one example, 502 indicates the first time for the current usage where the user places patch 100 on a portion of the body and manually adjusts the charge level, which is a series of charge pulses, until it feels suitable, or any time the charge level is changed, either manually or automatically. The treatment then starts. The mathematical expression of this function of the application of a charge is as follows:

The charge delivered in a treatment is $$Q_{target} = \sum_{i=1}^{T*f} Q_{pulse}(i)$$

Where T is the duration; f is the count of pulses for one treatment (e.g., Hertz or cycles/second) of "Rep Rate"; $Q_{pulse}(i)$ is the measured charge delivered by Pulse (i) in the treatment pulse train provided as a voltage MON_CURRENT that is the result of a Differential Integrator circuit shown in FIG. 6 (i.e., the average amount of charge per pulse). Differential Integrator circuit 700 of FIG. 9 is an example of a circuit used to integrate current measured over time and quantify the delivered charge and therefore determine the charge output over a treatment pulse. The number of pulses in the treatment is T*f.

As shown in of FIG. 9, MON_CURRENT 760 is the result of the Differential Integrator Circuit 700. The Analog to Digital Conversion ("ADC") 710 feature is used to quantify voltage into a number representing the delivered charge. The voltage is measured between Electrode A 720 and Electrode B 730, using a Kelvin Connection 740. Electrode A 720 and Electrode B 730 are connected to a header 750. A reference voltage, VREF 770, is included to keep the measurement in range.

In some examples, Analog to Digital Conversion 710 is an internal feature of controller 270. In some examples, Analog to Digital Conversion 710 is an external component, which delivers its digital output value to a digital input port on Controller 270.

At 504 and 506, every pulse is sampled. In one example, the functionality of 504 and 506 lasts for 10 seconds with a pulse rate of 20 Hz, which can be considered a full treatment cycle. The result of Acquisition phase 500 is the target pulse charge of $Q_{target}$.

FIG. 10 is a table in accordance with one example showing the number of pulses per treatment measured against two parameters, frequency and duration. Frequency is shown on the Y-axis and duration on the X-axis. The adaptive protocol in general performs better when using more pulses. One example uses a minimum of 100 pulses to provide for solid convergence of charge data feedback, although a less number of pulses can be used in other examples. Referring to the FIG. 7, a frequency setting of 20 Hz and duration of 10 seconds produces 200 pulses.

The reproduction phase 520 begins in one example when the user initiates another subsequent treatment after acquisition phase 500 and the resulting acquisition of the baseline charge, $Q_{target}$. For example, a full treatment cycle, as discussed above, may take 10 seconds. After, for example, a two-hour pause as shown at wait period 522, the user may then initiate another treatment. During this phase, the adaptive protocol attempts to deliver $Q_{target}$ for each subsequent treatment. The functionality of reproduction phase 520 is needed because, during the wait period 522, conditions such as the impedance of the user's body due to sweat or air humidity may have changed. The differential integrator is sampled at the end of each Pulse in the Treatment. At that point, the next treatment is started and the differential integrator is sampled for each pulse at 524 for purposes of comparison to the acquisition phase $Q_{target}$. Sampling the pulse includes measuring the output of the pulse in terms of total electric charge. The output of the integrator of FIG. 6 in voltage, referred to as Mon_Current 760, is a direct linear relationship to the delivered charge and provides a reading of how much charge is leaving the device and entering the user. At 526, each single pulse is compared to the charge value determined in Acquisition phase 500 (i.e., the target charge) and the next pulse will be adjusted in the direction of the difference.

$$NUM\_PULSES = (T*f)$$

After each pulse, the observed charge, $Q_{pulse}(i)$, is compared to the expected charge per pulse.

$$Q_{pulse}(i) > Q_{target}/NUM\_PULSES?$$

The output charge or "VBOOST" is then modified at either 528 (decreasing) or 530 (increasing) for the subsequent pulse by:

$$dV(i) = G[Q_{target}/NUM\_PULSES - Q_{pulse}(i)]$$

where G is the Voltage adjustment Coefficient–determined empirically. The process continues until the last pulse at 532.

A safety feature assures that the VBOOST will never be adjusted higher by more than 10%. If more charge is necessary, then the repetition rate or duration can be increased.

In one example a boosted voltage circuit uses dedicated circuits to servo the boosted voltage. These circuits process voltage and/or current measurements to control the PWM duty cycle of the boosted voltage circuit's switch. The system controller can set the voltage by adjusting the gain of the feedback loop in the boosted voltage circuit. This is done with a digital potentiometer or other digital to analog circuit.

In one example, in general, the current is sampled for every pulse during acquisition phase 500 to establish target charge for reproduction. The voltage is then adjusted via a digital potentiometer, herein referred to as "Pot", during reproduction phase 520 to achieve the established target_charge.

The digital Pot is calibrated with the actual voltage at startup. A table is generated with sampled voltage for each wiper value. Tables are also precomputed storing the Pot wiper increment needed for 1 v and 5 v output delta at each pot level. This enables quick reference for voltage adjustments during the reproduction phase. The tables may need periodic recalibration due to battery level.

In one example, during acquisition phase 500, the data set=100 pulses and every pulse is sampled and the average is used as the target_charge for reproduction phase 520. In general, fewer pulses provide a weaker data sample to use as a basis for reproduction phase 520.

In one example, during acquisition phase 500, the maximum data set=1000 pulses. The maximum is used to avoid overflow of 32 bit integers in accumulating the sum of samples. Further, 1000 pulses in one example is a sufficiently large data set and collecting more is likely unnecessary.

After 1000 pulses for the above example, the target_charge is computed. Additional pulses beyond 1000 in the acquisition phase do not contribute to the computation of the target charge. In other examples, the maximum data set is greater than 1000 pulses when longer treatment cycle times are desired.

In one example, the first 3-4 pulses are generally higher than the rest so these are not used in acquisition phase 500. This is also accounted for in reproduction phase 520. Using these too high values can result in target charge being set too high and over stimulating on the subsequent treatments in reproduction phase 520. In other examples, more advanced averaging algorithms could be applied to eliminate high and low values.

In an example, there may be a safety concern about automatically increasing the voltage. For example, if there is poor connection between the device and the user's skin, the voltage may auto-adjust at 530 up to the max. The impedance may then be reduced, for example by the user pressing the device firmly, which may result in a sudden high current. Therefore, in one example, if the sample is 500 mv or more higher than the target, it immediately adjusts to the minimum voltage. This example then remains in reproduction phase 520 and should adjust back to the target current/charge level. In another example, the maximum voltage increase is set for a single treatment (e.g., 10V). More than that is not needed to achieve the established target_charge. In another example, a max is set for VBOOST (e.g., 80V).

In various examples, it is desired to have stability during reproduction phase 520. In one example, this is accomplished by adjusting the voltage by steps. However, a relatively large step adjustment can result in oscillation or over stimulation. Therefore, voltage adjustments may be made in smaller steps. The step size may be based on both the delta between the target and sample current as well as on the actual VBOOST voltage level. This facilitates a quick and stable/smooth convergence to the target charge and uses a more gradual adjustments at lower voltages for more sensitive users.

The following are the conditions that may be evaluated to determine the adjustment step.

delta–mon_current=abs(sample_mon_current–target_charge)

If delta_mon_current>500 mv and $V_{BOOST}$>20V then step=5V for increase adjustments
(For decrease adjustments a 500 mv delta triggers emergency decrease to minimum Voltage)
If delta_mon_current>200 mv then step=1V
If delta_mon_current>100 mv and delta_mon_current>5%*sample_mon_current then step=1V In other examples, new treatments are started with voltage lower than target voltage with a voltage buffer of approximately 10%. The impedance is unknown at the treatment start. These examples save the target_voltage in use at the end of a treatment. If the user has not adjusted the strength parameter manually, it starts a new treatment with saved target_voltage with the 10% buffer. This achieves target current quickly with the 10% buffer to avoid possible over stimulation in case impedance has been reduced. This also compensates for the first 3-4 pulses that are generally higher.

As disclosed, examples apply an initial charge level, and then automatically adjust based on feedback of the amount of current being applied. The charge amount can be varied up or down while being applied. Therefore, rather than setting and then applying a fixed voltage level throughout a treatment cycle, implementations of the invention measure the amount of charge that is being input to the user, and adjust accordingly throughout the treatment to maintain a target charge level that is suitable for the current environment.

The Adaptive Circuit described above provides the means to monitor the charge sent through the electrodes to the user's tissue and to adjust the strength and duration of sending charge so as to adapt to changes in the impedance through the electrode-to-skin interface and through the user's tissue such that the field strength at the target nerve is within the bounds needed to overcome the action potential of that nerve at that location and activate a nerve impulse. These changes in impedance may be caused by environmental changes, such as wetness or dryness of the skin or underlying tissue, or by applied lotion or the like; or by tissue changes, such as skin dryness; or by changes in the device's placement on the user's skin, such as by removing the patch and re-applying it in a different location or orientation relative to the target nerve; or by combinations of the above and other factors.

The combined circuits and circuit controls disclosed herein generate a charge that is repeated on subsequent uses. The voltage boost conserves battery power by generating voltage on demand. The result is an effective and compact electronics package suitable for mounting on or in a fabric or similar material for adherence to a dermis that allows electrodes to be placed near selected nerves to be activated.

Adaptive Waveform for Fine Intensity Control

The oscillator clock frequency in example inventions is chosen to optimize power consumption of the clocked circuits while also providing enough speed for microcontroller operation and other timing circuits that are disclosed above.

PWM circuit 244 modifies the pulse width by varying the count of oscillator clock periods. Due to the limited clock frequency, it can be difficult to have enough resolution in the PWM duty cycle to create enough different strength levels in the stimulation. This may lead to users being unable to select between one level that is too weak and the next higher level that is too strong.

Therefore, in example inventions, control of the boosted voltage ($V_{BOOST}$) is enhanced to provide higher discernment between levels by foregoing level selection within the PWM duty cycle and instead initiating the stimulation at the moment the boosted voltage ramps to the desired voltage, as read by the microcontroller ADC. This achieves many more strength levels with smaller gaps between the levels than those, which are limited by the resolution of the PWM due to the much higher ADC measurement frequency. The ADC feedback to the microcontroller is used to curtail the PWM active time as soon as the desired voltage threshold is reached.

In addition to providing more levels of intensity adjustment, battery power is saved by stopping the boosted voltage output until the next pulse is needed. Some battery types have poor performance when the rate of change of the current demanded from the battery exceeds a certain maximum specification. A circuit, which begins to demand current from the battery and increases that demanded current level at a slower rate, allows the battery to perform better over multiple such cycles of demanded power.

In one example, the PWM duty cycle is varied from the first pulse to the last in the series of pulses for a stimulation, to use lower duty cycle pulses at the beginning of stimulation and higher duty cycle pulses later in the stimulation. The narrower pulses formed from the lower duty cycle reduce the demand for charge on the battery circuit, such that the current demand starts out more slowly than in a circuit without duty cycle adaptation, and continues through the stimulation pulse sequence to provide wider pulses with higher current demand, in order to stay within the current specification of the battery while also rising to meet the stimulation energy required by the user when they adjusted the intensity.

Qualifying Applied Stimulation Pulses

The energy provided by the battery for each stimulation pulse is dependent on the type of battery in patch 100. The performance of the battery changes during the course of applying the sequence of pulses. The battery performance may be affected by temperature, humidity, age of the battery, and other factors. Due to this variation in battery performance, in example inventions the treatment is adjusted most or every time the treatment is applied to a user.

Figure 11:
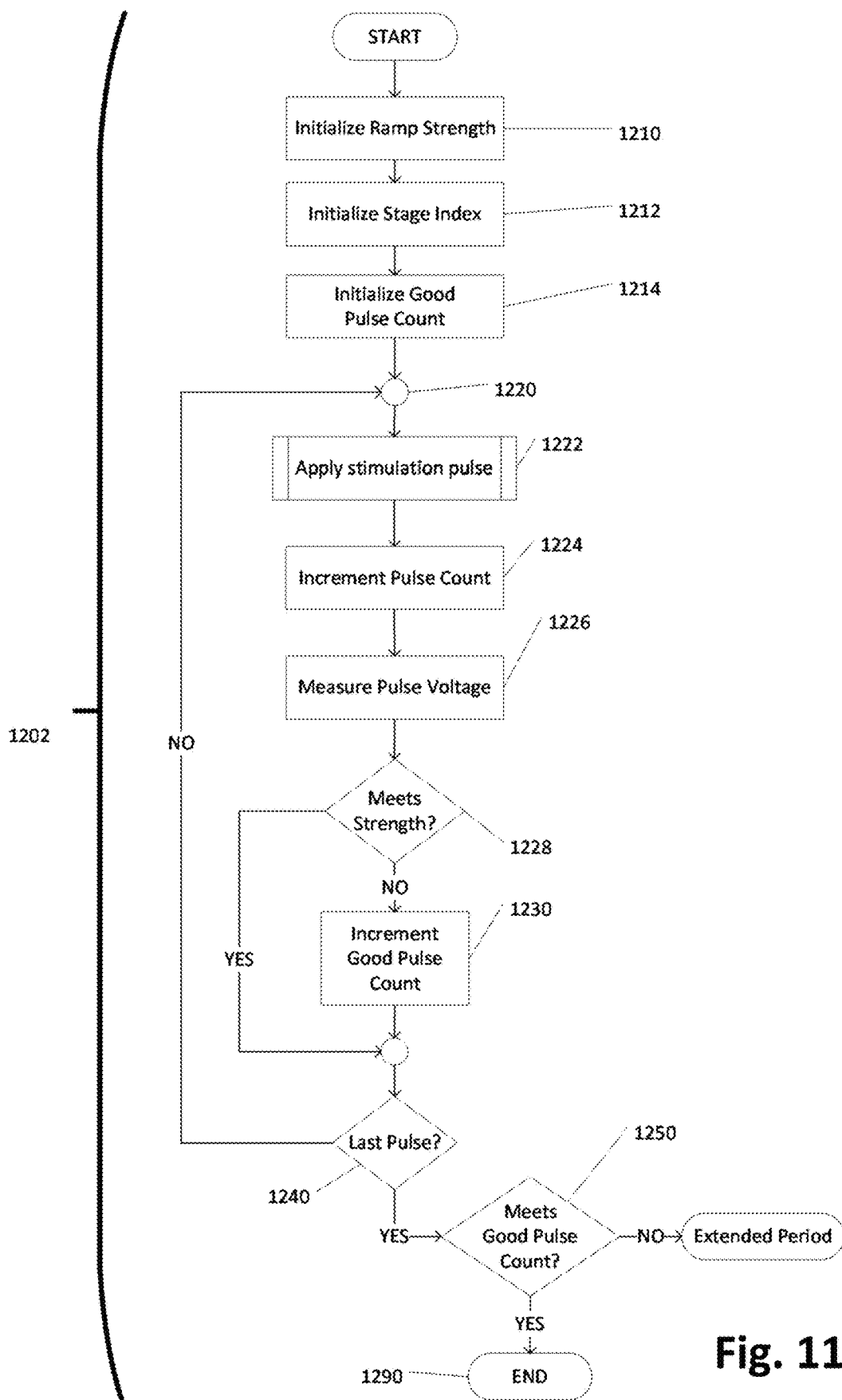
FIGS. 11 and 12 are flow diagrams of treatment monitoring functionality in accordance to example inventions.
Figure 12:
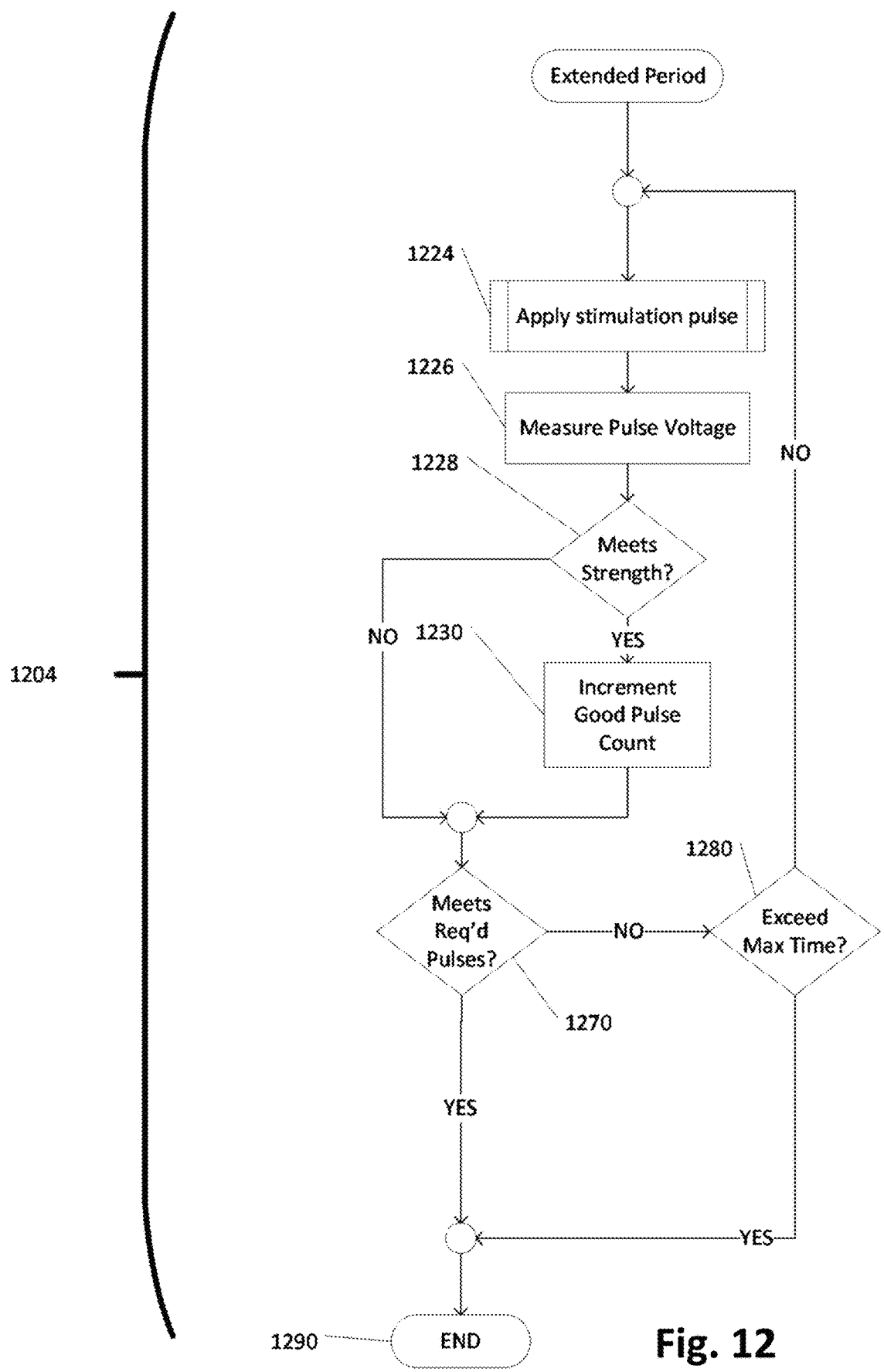

FIGS. 11 and 12 are flow diagrams of treatment monitoring functionality in accordance to example inventions. FIG. 11 is directed to a "normal" treatment monitoring process 1202, and begins with an initialization of ramp strength at 1210, and an initialization of a stage index at 1212 before treatment begins, followed by a normal application loop at 1220. Each iteration of the loop at 1220 applies a stimulation pulse at 1222, increments the pulse count at 1224 and then measures the pulse voltage at 1226. Each pulse amplitude is tested against a strength setting at 1228. In example inventions, the strength level is 1-20, producing voltages from 4V to 85V. Pulses, which do not achieve the target amplitude, are counted at 1230. A "good" pulse count is the number of pulses that meet the strength level, and a missed pulse count is the number of pulses minus the good pulse count. When the last treatment pulse has been applied at 1240, the count of missed pulses is compared to the missed pulse limit at 1250.

FIG. 12 is directed to an "extended" treatment monitoring functionality 1204 if at 1250 of FIG. 11 the amount of good pulse counts is not met. If more pulses have missed the target amplitude than are allowed by the missed pulse limit, then one or more extended treatment pulses at 1260 are applied. These pulses are added to the pulse count in the original treatment of FIG. 11, thereby lengthening the treatment time. When sufficient extended treatment pulses are applied to fulfill the number of necessary strength pulses at 1270, then the treatment completion at 1290 is achieved.

In example inventions, the target nerve stimulation pulse amplitude is set by one or more of the user, the firmware in patch 100, or the smart controller. To deliver at least the minimum number of pulses required for a treatment, patch 100 measures the amplitude of each applied stimulation pulse (i.e., the voltage level). A "normal" treatment is delivered in a fixed length of time. Each pulse, which does not achieve the target amplitude, is not counted as one of the pulses for the treatment minimum pulse count. When the normal treatment time has elapsed, patch 100 checks if the number of sufficiently strong pulses has met the minimum pulse count limit. If it has, the treatment is finished. If it has not, then additional pulses are applied to complete the treatment using the functionality of FIG. 12, thereby extending the duration of the treatment. If this extension exceeds a maximum treatment time at 1280, then the treatment is stopped at treatment completion 1290, even if the minimum number of applied strong pulses has not been met.

Patch 100 logs the counts of applied pulses, strong pulses, treatment time, and other parameters. This collected data may be transmitted to the smart controller or to another data storage device for later analysis.

Firmware Construction

As shown in FIG. 2, patch 100 includes control unit 1002. The set of features in control unit 1002 is used to provide control of the functions of patch 100 is the set of features most common across the set of specific control chips used for control unit 1002.

Differences in features offered on each of several chips available to build control unit 1002 results in an increase in firmware complexity when the firmware is designed to use a different set of features on each offered chip. This increase in complexity results in an increase in firmware problems across the set of patch 100s built on multiple chips, and increases the frequency of firmware updates needed to be delivered to that set of patch 100s. This increase in problems and updates limits the functionality of patch 100s in a subset of those users activating patch 100s on themselves.

By implementing function in the firmware using features compatible across the larger set of available chips, the complexity of the code, the frequency of firmware problems, and the frequency of firmware updates are reduced in example inventions.

In one example, between two different chips available as alternatives for control unit 1002, one chip provides interrupt service while in parallel performing analog to digital conversions in one or more peripherals such as ADCs. A second chip provides both interrupt service and ADC conversions, but not simultaneously or in parallel. Therefore, the patch 100 firmware is implemented using timer-based code rather than interrupt-based code, so that the same firmware may be executed on either of the two chips, thereby reducing the code to one compatible implementation.

In one example, between two different chips available as alternatives for control unit 1002, one chip provides support for many command types in the BLE wireless communication and a second chip provides support for only the lowest level BLE commands. Therefore, the firmware of patch 100 is implemented using only the lowest level BLE commands, such as single-write and single-read commands, thereby reducing the code to one compatible implementation.

BLE command coding bit errors when decoding commands received as byte values across the link between the smart controller or fob, and patch 100, can cause problems or latency delays in handling functions as requested by the smart controller or fob, such as writing data or reading data back, or initiating or terminating a function in patch 100. These bit errors are sometimes the result of weak signal quality between patch 100 and the smart controller or fob. The distances between these devices vary according to the habit of the user.

Patch 100 measures the receiving signal strength across BLE and quantifies it as a Received Signal Strength Indicator ("RSSI") binary value. The smart controller and/or fob requests these measured values using one or more of the BLE commands implemented in patch 100 and the smart controller and/or fob firmware. The smart controller and/or fob send these measured values to a computer or server or to the cloud to be analyzed. The analysis may correlate RSSI levels with retransmission rates of commands or data, and may calculate statistics for BLE function across a large population of patch 100s. These statistics and correlations are used to change the firmware and/or hardware designs of the smart controller, the fob or patch 100, to improve reliability and responsiveness.

BLE command opcodes are designed to minimize undetected bit errors when a command is received by patch 100. For each opcode with a binary pattern, there is a related opcode with the opposite binary pattern. Command opcodes, which differ by only one bit, are avoided.

Stack-Up of the Patch

Figure 13:
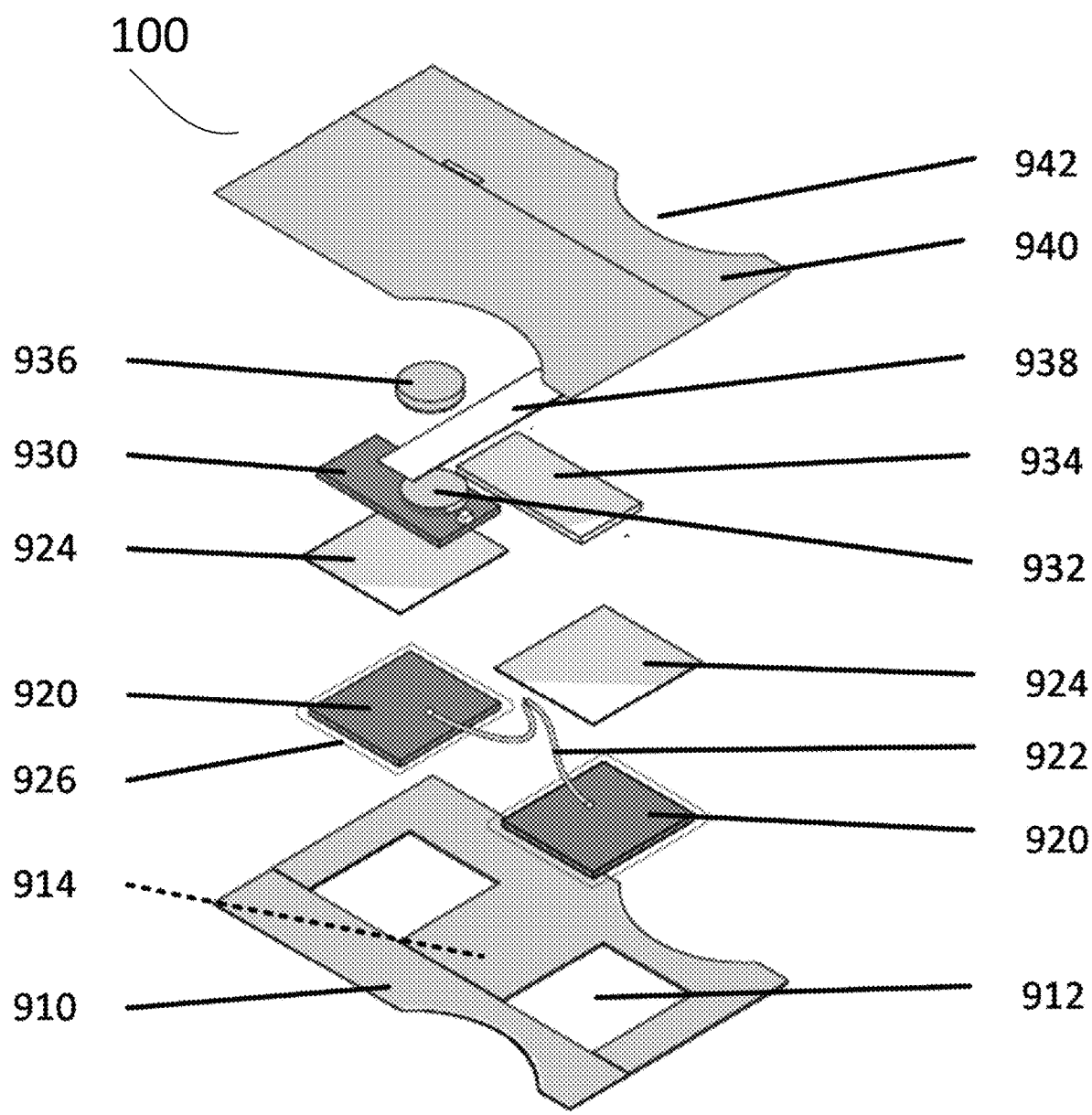
FIG. 13 illustrates a stack-up view of the patch in accordance with example inventions.

FIG. 13 illustrates a stack-up view of patch 100 in accordance with example inventions. A bottom layer 910 is a fabric tape with adhesive on the skin-facing side. A hole 912 is cut into the bottom layer for each of the electrodes 920. A removable paper 914 adheres to the adhesive on the skin-facing side of bottom layer 910. Two or more electrodes 920 are coupled by a wire 922 to a printed circuit board assembly ("PCBA") 930.

Electrodes 920 are covered with a polyimide tape A 924 to prevent short circuits from electrodes 920 to PCBA 930 and to prevent movement of electrodes 930 within the layers of the assembly. Each electrode 930 is coated on the skin-facing surface with hydrogel 926. Each electrode 920 has a release layer covering hydrogel 926. A battery clip 932 is attached to PCBA 930. A battery 936 is inserted into battery clip 932. A battery pull-tab 938 is inserted into battery clip 932. PCBA 930 is wrapped in polyimide tape B 934 to restrict access by the user to the electronics. A top layer 940 of fabric tape with adhesive on the PCBA-facing side is stacked on top to complete the assembly. Anklebone cutouts 942 are designed into the shapes of bottom layer 910 and top layer 940 to accommodate the ankle bone and to assist the user to correctly place patch 100.

Hydrogel Adaptation

Variations in the viscosity and composition of hydrogel 926 leads to variation in the migration of the substance from its original area on each electrode to a wider area, possibly touching the skin outside the dimensions of patch 100. As the hydrogel migrates, its electrical performance changes. The circuitry on PCBA 930 measures the voltage applied to the skin in real-time during the course of each treatment. The adaptive circuit calculates the charge delivered to the skin, which is a function of many parameters, including the conductivity of hydrogel 926. Therefore, the performance of patch 100 is maintained while the hydrogel portion of the device changes its performance. The adaptive circuit adjusts the delivery of charge to also account for all changes in body and skin conductivity, perspiration and patch contact.

As the performance of the hydrogel 926 decreases with time, the adaptive circuit and the firmware in PCBA 930 records the expected life of the specific patch while it is powered on and on the skin of the user. When patch 100 determines that the device's lifetime is near an end, the firmware signals to the fob or smart controller, such that the user receives an indication that this patch has reached its limit.

Crimped Connection from Electrode to PCBA

Each electrode 920 is coated with hydrogel 926 when the electrode is manufactured. In some examples, a wire 922 is connected to both the electrode and the PCBA 930 in a permanent fashion, such as by soldering, when electrodes 920 are manufactured. The electrode-plus-wire-plus-PCBA assemblies are each enclosed in an airtight bag until they are subsequently assembled with the tapes and adhesive layers to form a complete patch 100. Due to the complex nature of these assembly steps, the hydrogel on the electrodes may be exposed to air and humidity for a period of time, which affects the life expectancy of the hydrogel.

In an example, electrodes 920 are coated with hydrogel 926 but no wire is attached at that stage. Instead, a small clip is soldered to each electrode, which does not affect the hydrogel nor attach the electrode to any larger assembly, which would require longer time in the assembly line. These coated electrodes are each encased in an airtight bag with a heat seal or other means. The hydrogel does not degrade during the time that the coated electrode is inside the sealed bag.

In an example, wire 922 is inserted into the small clip which had previously been soldered to electrode 920, this connection being stronger and less prone to defect than the soldering or attachment of the wire strands directly to electrode 920. The clip and the wire do not affect hydrogel 926. Each coated electrode 920, with its clip and attached wire, is encased in an airtight bag with a heat seal or other means. Hydrogel 926 does not degrade during the time that the coated electrode is inside the sealed bag. The coated electrodes 920 are removed from their airtight bags only immediately before they are connected to PCBA 930.

An additional benefit of separating the coated electrodes 920 from PCBA 930 as two different subassemblies until put into a completed patch 100 is that coated electrodes found to be defective or expired from too lengthy time on the shelf may be discarded without the expense of discarding an already-attached PCBA. The more expensive PCBAs have a shelf life independent of the shelf life of the coated electrodes. These two subassemblies' inventories may be stocked, inspected and managed independently. This reduces the overall cost of manufacture of patches 100 devices without affecting their performance.

Die Cut Fabric Tape

In some examples, bottom layer 910 is placed as a layer over electrodes 920 using a solid layer of fabric tape. The overall thickness of patch 100 is therefore partly determined by the thickness of the fabric tape over electrodes 920. Further, in order to place electrodes 920 on the layer of fabric tape securely, the paper cover on the fabric tape must be pulled back to expose the adhesive coating. This results in a degradation of the adhesive properties of the tape.

In examples of patch 100, bottom layer 910 fabric tape is cut to create holes 912 for each of electrodes 920, according to the defined sizes of those components. Each electrode 920 is placed in the corresponding hole, without the added thickness of a fabric tape layer on top. Since no paper cover needs to be pulled back to mount electrodes 920 to the fabric tape, the adhesive of the fabric tape is not affected. The holes may be cut with a die in order to create accurate edges, without tears or fibers, which may interfere with electrodes 920.

Contoured to Ankle Bone

In some examples, patch 100 has a rectangular shape. This allows PCBA 930, battery 936 and electrodes 920 to fit in between fabric and adhesive bottom layer 910 and top layer 940, and to be affixed to the skin by the user, then to be peeled away and discarded after use. In some examples, patch 100 has a shape contoured to the position in which it is to be affixed to the skin. The reference point in properly positioning patch 100 is the malleolus, or ankle bone in some example uses. Therefore, patch 100 has an anklebone cutout 942 along the vertical side, this cutout accommodating the anklebone when patch 100 is placed close alongside the anklebone.

In some examples, cutout 942 is designed into patch 100 on only one side, such that battery 936, PCBA 930 and electrodes 920 are properly aligned on one of the left or the right ankle. Patch 100 can then be offered in two varieties—one for the left ankle with cutout 942 on the first vertical side, and one for the right ankle with cutout 942 on the second vertical side.

In some examples, cutout 942 is designed into patch 100 on both vertical sides, such that battery 936, PCBA 930 and electrodes 920 are properly aligned on either of the left or right ankle. Patch 100 can then be offered in only one variety.

Battery and Battery Tab

Patch 100 includes battery 936, which is enclosed by battery clip 932, assembled onto PCBA 930. During manufacturing, battery 936 is inserted into battery clip 932 to secure it from dropping out. In addition to the battery itself, battery pull-tab 938 is placed between one contact of battery 936 and the corresponding contact in battery clip 932. Battery pull-tab 938 prevents electrical connection between battery 936 and battery clip 932 at that contact until battery pull-tab 938 is removed. When in place, there is an open circuit such that patch 100 is not activated and does not consume power until battery pull-tab 938 is removed.

In some examples, battery pull-tab 938 is designed to be removed by pulling it out in the direction opposite that in which battery 936 was inserted into battery clip 932. This pulling action may lead to movement of the battery itself since it experiences a pulling force toward the open side of battery clip 932. This battery movement may cause patch 100 to cease operating or to never activate.

In one example, battery pull-tab 938 and battery clip 932 are designed so that battery pull tab 938 is pulled out in the same direction as battery 936 was pushed into battery clip 932. Therefore, the force pulling battery pull-tab 938 out of patch 100 serves only to make battery 936 more secure in its battery clip 932. This reduces the chance of inadvertent movement of battery 936 and the effect on activation or operation of patch 100.

Electrode Release Film

Each of electrodes 920 in the assembled patch 100 is covered with a Polyethylene Terephthalate ("PET") silicon covered release film 926. The release film is pulled away by the user when patch 100 is affixed to the skin. In some examples, the PET silicon covered release film 926 is transparent. This may lead to instances of confusion on the part of the user when the user may not be able to determine if the tape has been removed or not. Affixing patch 100 to the skin with any of electrodes 920 still covered with tape will cause patch 100 to be ineffective. This ineffectiveness may not be noticed until the first treatment with patch 100. If the affixed patch 100 is found to be ineffective when the user is feeling an urge to urinate, the user may struggle to either properly void their bladder or to remove patch 100, peel off the tapes from the electrodes or affix a new patch 100 and suppress the urge with the re-affixed or new device.

In examples, PET silicon covered release film 926 covering electrodes 920 is selected in a color conspicuous to the user, such that the user will readily determine if the tape has been removed or not.

Examples use circuitry and firmware to stimulate the electrode circuit with a brief, low energy pulse or pulse sequence when patch 100 is initially activated. If patch 100 is activated before it is affixed to the skin, the electrode readiness test will fail. In such a case, the electrode readiness test is repeated, again and again according to timers in the firmware or hardware, until either the timers have all expired or the test passes. The test passes when patch 100 is found to exhibit a circuit performance appropriate to its design. The test fails when patch 100 is not properly prepared, such as not removing the electrode films, or is not yet applied to the skin when the timers have all expired. When the electrode readiness test fails, patch 100 signals to the fob or the smart controller, which in turn informs the user. The electrode readiness test is implemented in a manner which may be undetectable by the user, and to minimize the test's use of battery power.

Removable Paper

In some examples, a removable paper 914 covers the adhesive side of bottom layer 910. Removable paper 914 may be in multiple sections, each to be pulled away by the user when affixing patch 100 to the skin. These removable papers may be in addition to the piece of PET film 926 covering each electrode 920. Therefore, the user must remove all of these pieces to expose a complete, adhesive surface to affix to the skin in examples.

In examples, bottom layer 910 is one complete piece, with one removable paper 914. The user removes all of the removable paper in one motion. In examples, bottom layer 910 is two or more pieces, with two or more removable papers 914. The user removes all of the removable papers. In examples, the single removable paper 914 is designed with a pull-tab, so that the user pulls the removable paper off of the bottom layer in a direction at right angle to the long axis of patch 100. This motion reduces the forces experienced by the assembled internal components of patch 100.

In examples, removable paper 914 covers bottom layer 910 and covers all of the PET film sections 926. An adhesive attaches the removable paper top surface to the polyimide tape A skin-facing surface, such that the user pulls the removable paper away from the bottom layer and in one motion removes the PET film pieces from electrodes 920.

Patch 100 can also be made more comfortable by the addition of material between the top layer and the bottom layer, such as cushioning material that can cushion the electrodes and electronic components. The cushioning material may be disposed subjacent to the bottom layer and superjacent to the top layer, in at least a portion of patch 100. A cushioning material may include cellulosic fibers (e.g., wood pulp fibers), other natural fibers, synthetic fibers, woven or nonwoven sheets, scrim netting or other stabilizing structures, superabsorbent material, foams, binder materials, or the like, as well as combinations thereof.

Hydrogel Overlaps Electrode Edges

In some examples, each electrode 920 is covered with hydrogel 926, which conforms to the size of the electrode 920, such that the edge of electrode 920 is exposed to the user's skin when patch 100 is applied to the skin. This edge may abrade or cut the user's skin during the time when patch 100 is affixed to the skin.

In some examples, hydrogel 926 is dimensioned so as to overlap the edges of electrode 920. Hydrogel 926 is placed over electrode 920 with the accuracies of placement used in manufacturing, such that the edges of electrode 920 is always covered with hydrogel 926. This keeps the edge electrode 920 from touching the user's skin. The risk of electrodes 920 from abrading or cutting the user's skin is therefore eliminated.

Figure 14:
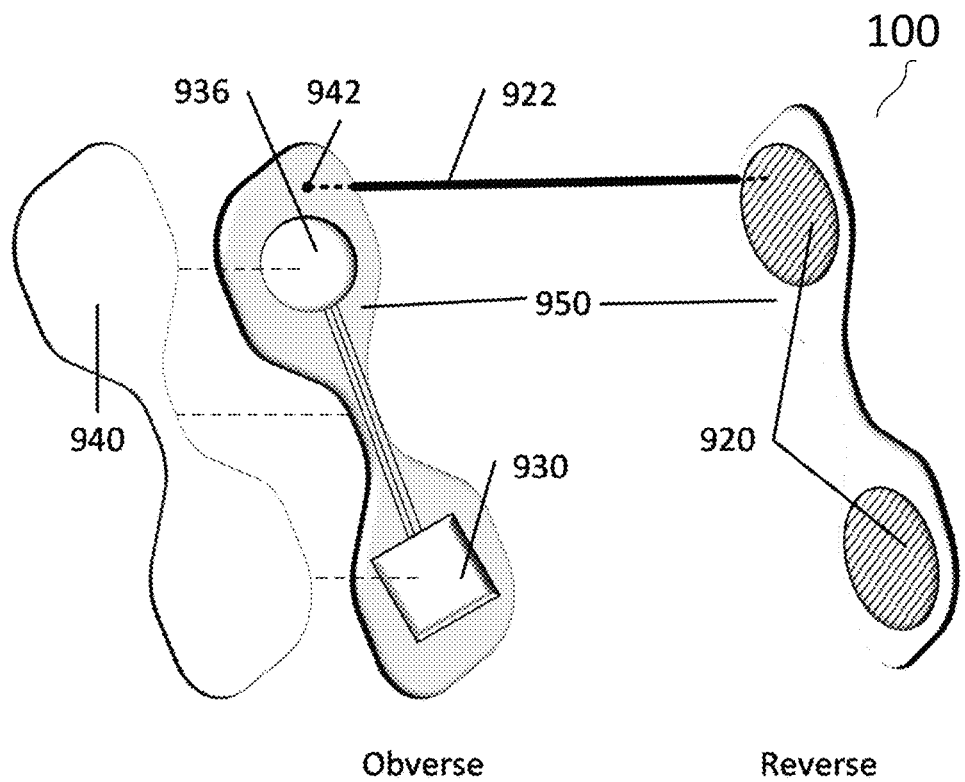
FIG. 14 illustrates a stack-up view of the patch in accordance with example inventions as assembled onto a substrate.

FIG. 14 illustrates a stack-up view of patch 100 in accordance with example inventions as assembled onto a substrate 950. Battery 936 is affixed to substrate 950 directly or via a battery clip, and connected to the electronics using two or more conducting paths plated onto substrate 950. Electrodes 920 are connected to the voltage and ground using vias 942, creating electrical paths from the top surface to the bottom surface of substrate 950. A top layer 940 is affixed over battery 936 to restrict access by the user to the electronics.

The distance between electrodes 920 may be selected to maximize the effectiveness of the electrical signal at the target nerve and/or minimize the footprint of patch 100. Each electrode 920 may have a body-facing surface area of from about 500 mm$^2$ to about 1100 mm$^2$. Electrodes 920 may have different or identical body-facing surface areas. The sum of the body-facing surface areas of the electrodes 920 may be less than 3,000 mm$^2$, preferably from about 1050 mm$^2$ to about 2200 mm$^2$, more preferably from about 500 mm$^2$ to 2200 mm$^2$.

Electrodes 920 may be spaced about 1 mm apart to about 100 mm apart (edge to edge), preferably about 5 mm apart to about 80 mm apart, more preferably about 10 mm apart to about 60 mm apart. The distance between the electrodes 920 may be selected to maximize the effectiveness of the electrical signal at the target nerve and/or minimize the footprint of the nerve stimulation device. Alternatively, patch 100 may include an array of electrodes. Further, as shown in FIG. 14, electrodes 920 are spaced apart by a relatively narrow isthmus 925. Isthmus 925 provides separation of electrodes 920 to enhance performance, and provides enhance wearing comfort and reduces wear during prolonged use for patch 100, particularly when patch 100 is placed on the ankle. Further, isthmus 925 relieves strain and the breaking of leads between the circuit and the battery, or other components.

Matrix Pattern in Electrodes

Figure 15:
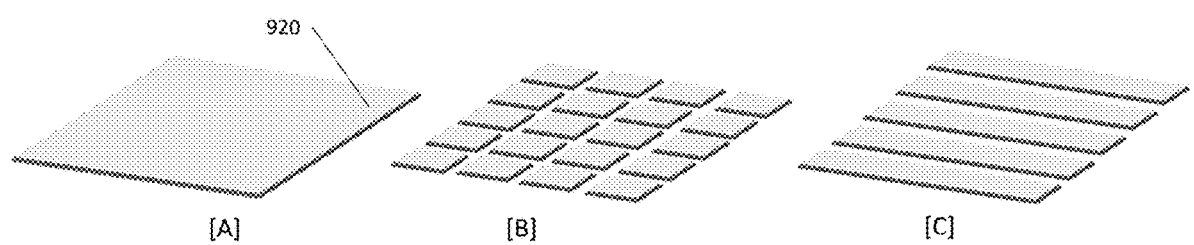
FIG. 15 illustrates solid and patterned electrodes that are used in different examples of the patch.

FIG. 15 illustrates solid and patterned electrodes that are used in different examples of patch 100. In an example, each of the two electrodes 920 is plated onto a substrate layer as a continuous area, as shown in FIGS. 14 and 15A.

In one example, each of the two electrodes 920 is plated in a matrix pattern, as shown in FIG. 15B, such that the surface of each electrode is planar. The ripples seen when using a continuous, plated area are absent, and the electrode lies flat against the user's skin. Each of the elements of the matrix is connected to a common electrical junction, which is driven by the activation voltage, such that the activation voltage is driven to all elements of the matrix simultaneously.

In one example, each of the two electrodes 920 is plated in a striped pattern, as shown in FIG. 15C, such that the surface of each electrode is planar. Each of the elements of the striped pattern is connected to a common electrical junction which is driven by the activation voltage, such that the activation voltage is driven to all elements of the matrix simultaneously. The common electrical junction may be in a layer of the PCB separate from the outer plated layer, or the junction may be formed by connecting the stripes around their perimeter or from stripe to stripe at midpoints.

In one example, a printed circuit board assembly ("PCBA") 930 (e.g., the use of one or both sides of the PCB, whether rigid or flexible, for the plating of conductive paths and the mounting of electronic components) is assembled onto a flexible substrate rather than a rigid substrate, as shown in FIG. 14, such that the ripples seen when using a rigid substrate are absent, and the PCBA lies flat against the User's skin.

The overall area of the electrode in matrix or striped form is calculated to provide sufficient coverage on the User's skin to allow for variations in placement of the electrode over the target location for nerve activation, such that, even if patch 100 is placed off-center from the optimum location, the electrodes extend across the target area sufficiently to deliver effective stimulation.

A layer of Hydrogel 926 coats each of electrodes 920 in example inventions. Although electrodes 920 are plated in a matrix or striped or similar pattern, the Hydrogel is a continuous area across each of the two Electrodes. This continuous conductive surface distributes the applied pulse voltage across an area of skin to avoid disturbing the surface of the skin.

Protection of Circuit Components

The layer of Hydrogel 926 coats the electrode side of PCBA 930. Vias are used to connect from the top surface of the PCB to the bottom surface, providing electrical connections for one or more of the components such as the SOC 1000. During use of patch 100, the Hydrogel may migrate through one or more of the vias to the top surface of the PCB. This migrated material, being conductive, may interfere with the performance of the one or more electrical components on the top surface of the PCB, such as causing a short circuit to ground or other voltage on one or more pins of such components, an example being the SOC 1000.

The PCB is manufactured with a layer covering the one or more through vias, this layer being affixed to the bottom side of the PCB. Hydrogel 926 is coated to the bottom side of the PCB after the application of the covering layer on the vias. The covering layer prevents the ingress and migration of Hydrogel or other contaminants such as water into and/or through the vias, thereby forming a permanent barrier so that the functionality of patch 100 is maintained through repeated use by the user. This covering layer also prevents ingress and migration during the time from manufacture to initial use by the User, thereby assuring shelf life of patch 100.

Hydrogel Impedance

The power required to perform a stimulation is related to the applied voltage and the impedance seen by electrodes 920 through Hydrogel 926 and the user's skin. When the Hydrogel has a higher impedance, more power is required to perform a stimulation. With the fixed power available from battery 936 in patch 100, this energy per stimulation sets a limit to the number of stimulations, which may be applied.

In an example, a Hydrogel 926 with a lower impedance has been selected to allow for less energy dissipated in the circuit, and more stimulations per patch 100 using battery 936. The Hydrogel's impedance may be minimized by one or more of reducing the Hydrogel coating thickness, changing the material composition, and increasing the size of the Hydrogel coating onto electrodes 920 even extending beyond the borders of the Electrodes onto the bottom surface of the PCBA 930.

Voltage Doubler Circuit

In one example, a voltage doubler circuit, using two diode stages, is added to boosted voltage circuit 200 of FIG. 2 to double the high voltage output or to reduce voltage stress on FET 242. The voltage doubler circuit builds charge in a transfer capacitor when FET 242 is turned on and adds voltage to the output of boosted voltage circuit 200 when FET 242 is turned off. The diodes only conduct in the positive phase so that the voltage is doubled.

Figure 16:
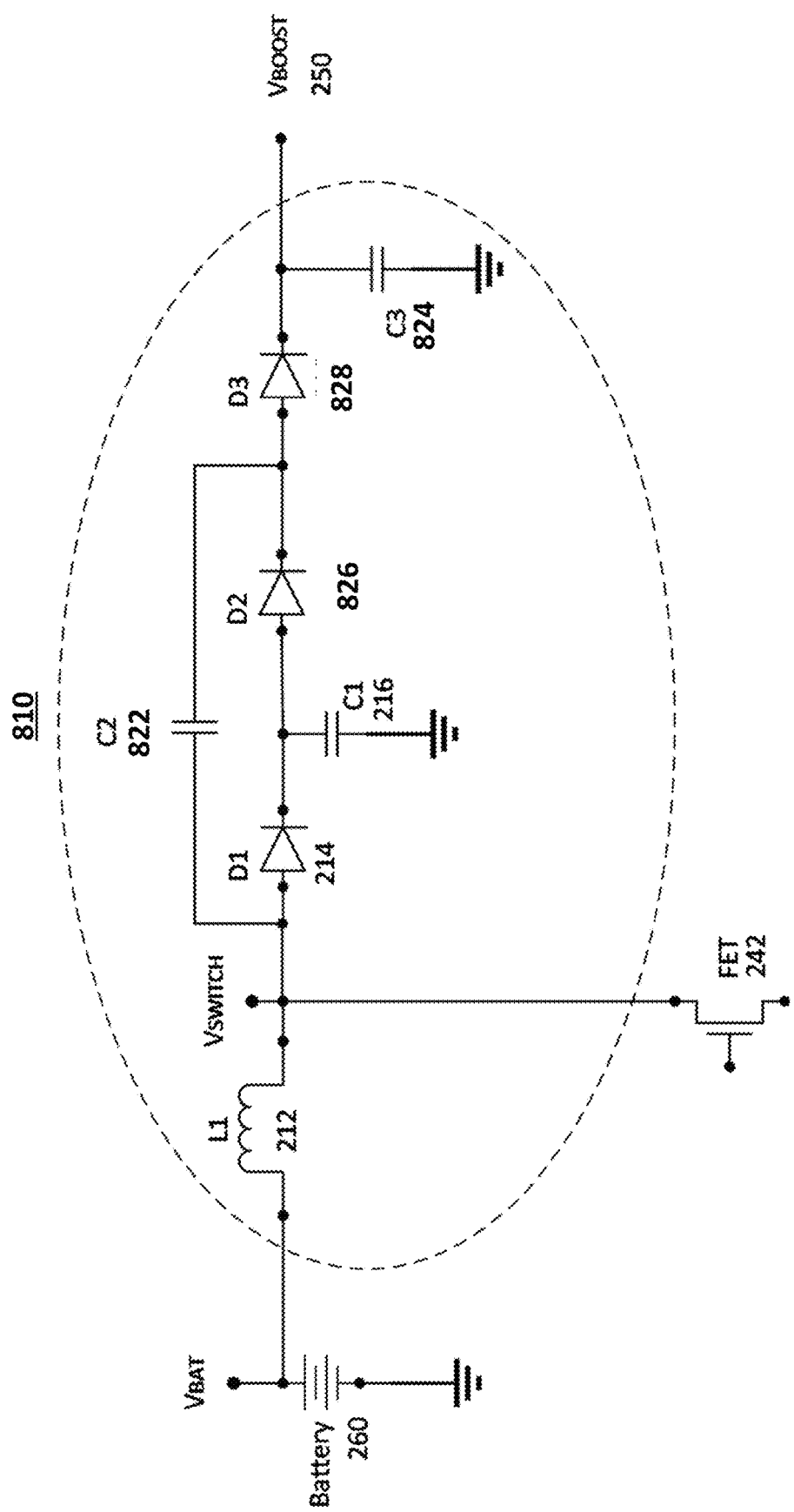
FIG. 16 illustrates a boosted converter circuit that can be used instead of the boosted converter circuit in boosted voltage circuit of FIG. 2 in example inventions.

FIG. 16 illustrates a boosted converter circuit 810 that can be used instead of boosted converter circuit 210 in boosted voltage circuit 200 of FIG. 2 in example inventions. Boosted converter circuit 810 includes three diode stages with the addition of diodes 826, 828 and capacitors 822, 824. In other example, even more stages similar to the addition of diodes 826, 828 and capacitors 822, 824 can be added to further boost voltage if needed.

As disclosed, example inventions include a topical nerve stimulation patch that includes a substrate, a dermis conforming bottom surface of the substrate comprising adhesive and adapted to contact a dermis of a user, a top outer surface of the substrate approximately parallel to the bottom surface, a plurality of electrodes positioned on the patch proximal to the bottom surface and located beneath the top outer surface and coupled to the substrate, a power source and electronic circuitry embedded in the patch and located beneath the top outer surface and coupled to the substrate. The electronic circuitry is configured to generate an electrical stimuli via the electrodes that comprise a plurality of pulses of a target output voltage. The electronic circuitry includes a controller configured to generate a first pulse at a first output voltage that is less than the target output voltage and generate a second pulse at a second output voltage that is less than the target output voltage and greater than the first output voltage.

In example invention, the controller is further configured to generate a plurality of subsequent pulses at the target output voltage after the first pulse and the second pulse. The electronic circuitry further includes a switch that couples generated pulses to the electrodes, where the controller opens the switch during the generation of the first pulse and the second pulse so that the first pulse and the second pulse are not coupled to the electrodes and closes the switch during the generation of the subsequent pulses to that the subsequent pulses are coupled to the electrodes.

In example inventions, the controller is further configured to generate a plurality of additional pulses that are less than the target output voltage before generating the subsequent pulses. A first pulse period of the first pulse is different from a subsequent pulse period of the subsequent pulses.

In example inventions, the circuitry further includes a voltage monitor for determining an output voltage, the voltage monitor measuring the first output voltage before generating the second output voltage. The electronic circuitry further includes a pulse width modulation ("PWM") circuit configured to modify a width of one or more of a plurality of activation pulses during a PWM duty cycle.

In example inventions, the electronic circuitry further includes a boosted voltage circuit configured to ramp a voltage level of each of the pulses to a desired level. The controller is configured to stop the boosted voltage circuit output between pulses until a next pulse is needed.

In example inventions, the controller is configured to vary the PWM duty cycle during the plurality of activation pulses so that a lower PWM duty cycle is used at a beginning of the electrical stimuli to form relatively narrow pulses and a higher PWM duty cycle is used at an end of the electrical stimuli to form relatively wider pulses.

In example inventions, the electrical stimuli includes a pulse count and the controller is configured to determine during the generation of the plurality of activation pulses a count of a number of the activation pulses that achieve a predefined strength setting, and when the count does not exceed a predefined number, generating extra pulses to add to the pulse count.

Example inventions utilize a patch with the various functionality and circuitry disclosed herein. However, in other inventions, a form factor other than a patch may be implemented.

Several examples are specifically illustrated and/or described herein. However, it will be appreciated that modifications and variations of the disclosed examples are covered by the above teachings and within the purview of the appended claims without departing from the spirit and intended scope of the invention.

What is claimed is:

1. A topical nerve stimulation patch comprising:
    a substrate;
    a dermis conforming bottom surface of the substrate adapted to contact a dermis of a user;
    a top outer surface of the substrate approximately parallel to the bottom surface;
    a plurality of electrodes positioned on the patch proximal to the bottom surface and located beneath the top outer surface and coupled to the substrate;
    a power source comprising a battery having an amount of usable energy; and
    electronic circuitry embedded in the patch and located beneath the top outer surface and coupled to the substrate, the electronic circuitry configured to generate an electrical stimuli via the electrodes during a treatment period, the electrical stimuli comprising a plurality of pulses of a target output voltage comprising a pulse width modulation, the electronic circuitry comprising a controller configured to, during the treatment period:
        generate a first pulse at a first output voltage that is less than the target output voltage;
        generate a second pulse at a second output voltage that is less than the target output voltage and greater than the first output voltage; and
        generate a plurality of subsequent pulses at the target output voltage after the first pulse and the second pulse;
    wherein the generation of at least the first pulse and the second pulse before the subsequent pulses during the treatment period increases the amount of usable energy available for treatment periods by the patch.

2. The topical nerve stimulation patch of claim 1, wherein the first pulse is approximately 50% of the target output voltage and the second pulse is approximately 75% of the target output voltage.

3. The topical nerve stimulation patch of claim 2, the electronic circuitry further comprising a switch that couples generated pulses to the electrodes, the controller further configured to:
    open the switch during the generation of the first pulse and the second pulse so that the first pulse and the second pulse are not coupled to the electrodes; and
    close the switch during the generation of the subsequent pulses to that the subsequent pulses are coupled to the electrodes.

4. The topical nerve stimulation patch of claim 2, the controller further configured to:
    generate a plurality of additional pulses that are less than the target output voltage before generating the subsequent pulses.

5. The topical nerve stimulation patch of claim 2, a first pulse period of the first pulse is different from a subsequent pulse period of the subsequent pulses.

6. The topical nerve stimulation patch of claim 1, the circuitry further comprising a voltage monitor for determining an output voltage, the voltage monitor measuring the first output voltage before generating the second output voltage.

7. The topical nerve stimulation patch of claim 1, the electronic circuitry further comprising a pulse width modulation (PWM) circuit configured to modify a width of one or more of a plurality of activation pulses during a PWM duty cycle.

8. The topical nerve stimulation patch of claim 6, the electronic circuitry further comprising a boosted voltage circuit configured to ramp a voltage level of each of the pulses to a desired level.

9. The topical nerve stimulation patch of claim 8, the controller configured to stop the boosted voltage circuit output between pulses until a next pulse is needed.

10. The topical nerve stimulation patch of claim 7, the controller configured to vary the PWM duty cycle during the plurality of activation pulses so that a lower PWM duty cycle is used at a beginning of the electrical stimuli to form relatively narrow pulses and a higher PWM duty cycle is used at an end of the electrical stimuli to form relatively wider pulses.

11. The topical nerve stimulation patch of claim 7, the electrical stimuli comprising a pulse count, the controller configured to determine during the generation of the plurality of activation pulses a count of a number of the activation pulses that achieve a predefined strength setting, and when the count does not exceed a predefined number, generating extra pulses to add to the pulse count.

12. A method of stimulating a nerve of a user, the method comprising:
    attaching to the user a topical nerve activation patch, the patch comprising:
        a substrate;
        a dermis conforming bottom surface of the substrate adapted to contact a dermis of a user;
        a top outer surface of the substrate approximately parallel to the bottom surface;
        a plurality of electrodes positioned on the patch proximal to the bottom surface and located beneath the top outer surface and coupled to the substrate;
        a power source comprising a battery having an amount of usable energy; and electronic circuitry embedded in the patch and located beneath the top outer surface and coupled to the substrate, the electronic circuitry comprising a controller;

generating an electrical stimuli via the electrodes during a treatment period, the electrical stimuli comprising a plurality of pulses of a target output voltage comprising a pulse width modulation;

generating a first pulse at a first output voltage that is less than the target output voltage;

generating a second pulse at a second output voltage that is less than the target output voltage and greater than the first output voltage; and generating a plurality of subsequent pulses at the target output voltage after the first pulse and the second pulse;

wherein the generation of at least the first pulse and the second pulse before the subsequent pulses during the treatment period increases the amount of usable energy available for treatment periods by the patch.

13. The method of claim 12, wherein the first pulse is approximately 50% of the target output voltage and the second pulse is approximately 75% of the target output voltage.

14. The method of claim 13, the electronic circuitry further comprising a switch that couples generated pulses to the electrodes, further comprising:

opening the switch during the generation of the first pulse and the second pulse so that the first pulse and the second pulse are not coupled to the electrodes; and closing the switch during the generation of the subsequent pulses to that the subsequent pulses are coupled to the electrodes.

15. The method of claim 13, further comprising:

generating a plurality of additional pulses that are less than the target output voltage before generating the subsequent pulses.

16. The method of claim 13, a first pulse period of the first pulse is different from a subsequent pulse period of the subsequent pulses.

17. The method of claim 12, the circuitry further comprising a voltage monitor for determining an output voltage, the method further comprising measuring the first output voltage before generating the second output voltage.

18. The method of claim 12, the electronic circuitry further comprising a pulse width modulation (PWM) circuit, the method further comprising modifying a width of one or more of a plurality of activation pulses during a PWM duty cycle.

19. The method of claim 17, the electronic circuitry further comprising a boosted voltage circuit, the method further comprising ramping a voltage level of each of the pulses to a desired level.

20. The method of claim 19, further comprising stopping the boosted voltage circuit output between pulses until a next pulse is needed.

* * * * *